(12) United States Patent
Ye

(10) Patent No.: US 11,613,776 B2
(45) Date of Patent: Mar. 28, 2023

(54) MUTANT CELL-FREE DNA ISOLATION KIT AND MUTANT CELL-FREE DNA ISOLATION METHOD USING THE SAME

(71) Applicant: GENECKER CO., LTD, Seongnam-si (KR)

(72) Inventor: Sung Hyeok Ye, Daegu (KR)

(73) Assignee: GENECKER CO., LTD., Seongnam-si (KR)

( * ) Notice: Subject to any disclaimer, the term of this patent is extended or adjusted under 35 U.S.C. 154(b) by 479 days.

(21) Appl. No.: 16/637,412

(22) PCT Filed: Feb. 7, 2019

(86) PCT No.: PCT/KR2019/001518
§ 371 (c)(1),
(2) Date: Feb. 7, 2020

(87) PCT Pub. No.: WO2019/156475
PCT Pub. Date: Aug. 15, 2019

(65) Prior Publication Data
US 2020/0283841 A1    Sep. 10, 2020

(30) Foreign Application Priority Data

Feb. 6, 2018  (KR) .................. 10-2018-0014478
Feb. 1, 2019  (KR) .................. 10-2019-0013912

(51) Int. Cl.
| | | |
|---|---|---|
| C12Q 1/68 | (2018.01) | |
| C12N 9/22 | (2006.01) | |
| C12N 15/10 | (2006.01) | |
| C12Q 1/6858 | (2018.01) | |
| C12N 15/113 | (2010.01) | |
| C12Q 1/6886 | (2018.01) | |

(52) U.S. Cl.
CPC ............. *C12Q 1/6858* (2013.01); *C12N 9/22* (2013.01); *C12N 15/10* (2013.01); *C12N 15/113* (2013.01); *C12Q 1/6886* (2013.01); *C12N 2310/20* (2017.05); *C12N 2800/80* (2013.01)

(58) Field of Classification Search
CPC .............................. C12Q 1/6858; C12N 15/10
See application file for complete search history.

(56) References Cited

U.S. PATENT DOCUMENTS

| | | | |
|---|---|---|---|
| 2017/0211142 A1 | 7/2017 | Smargon et al. | |
| 2018/0127785 A1 | 5/2018 | Junge et al. | |
| 2018/0355417 A1* | 12/2018 | Shuber ................. | C12Q 1/6827 |

FOREIGN PATENT DOCUMENTS

| | | | | |
|---|---|---|---|---|
| CN | 107614680 A | 1/2018 | | |
| EP | 3 150718 A1 | 4/2017 | | |
| JP | 2016-520317 A | 7/2016 | | |
| JP | 2017-538427 A | 12/2017 | | |
| KR | 10-2015-0101446 A | 9/2015 | | |
| KR | 10-2016-0129523 A | 11/2016 | | |
| KR | 10-1815695 B1 | 1/2018 | | |
| WO | WO 2016/100955 A2 | 6/2016 | | |
| WO | WO-2016210224 A1 * | 12/2016 | ............. | C12N 15/10 |
| WO | WO 2017/155146 A1 | 9/2017 | | |
| WO | WO 2017/218512 A1 | 12/2017 | | |

OTHER PUBLICATIONS

Jia, Chenqiang, et al. "New applications of CRISPR/Cas9 system on mutant DNA detection." Gene 641 (2018): 55-62. (Year: 2018).*
Gu, Wei, et al. "Depletion of Abundant Sequences by Hybridization (DASH): using Cas9 to remove unwanted high-abundance species in sequencing libraries and molecular counting applications." Genome biology 17.1 (2016): 1-13. (Year: 2016).*
Nikiforov, Theo T., et al. "The use of phosphorothioate primers and exonuclease hydrolysis for the preparation of single-stranded PCR products and their detection by solid-phase hybridization." Genome Research 3.5 (1994): 285-291. (Year: 1994).*
Lee, Seung Hwan, st al. "CUT-PCR: CRISPR-mediated, ultrasensitive detection of target DNA using PCR." *Oncogene* 36.49 (Aug. 28, 2017): 6823-6829.
Gu, W., E. D. Crawford, and B. D. O'Donovan. "Depletion of Abundant Sequences by Hybridization (DASH): using Cas9 to remove." *Genome Biology* (Mar. 4, 2016): pp. 13.
Jia, Chenqiang, et al. "New applications of CRISPR/Cas9 system on mutant DNA detection." *Gene* vol. 641 (Oct. 12, 2017): 55-62.
Extended European search report dated Jan. 3, 2022 in counterpart European Patent Application No. 197515556.2 (6 pages in English).
International Search Report dated May 14, 2019 in corresponding International Patent Application No. PCT/KR2019/001518 (3 pages in English, 3 pages in Korean).
Jinek et al., "A Programmable Dual-RNA—Guided DNA Endonuclease in Adaptive Bacterial Immunity," Science, Aug. 17, 2012, 337, pp. 816-821.
Zalatan et al., "Engineering Complex Synthetic Transcriptional Programs with CRISPR RNA Scaffolds," Cell, Jan. 15, 2015, 160, pp. 339-350.
Tian et al., "Advancing high-throughput gene synthesis technology," Molecular Biosystem, 2009, 5(7), pp. 714-722.
Metzker, "Sequencing technologies—the next generation," Nature Reviews Genetics, vol. 11, Jan. 2010, pp. 31-46.

* cited by examiner

*Primary Examiner* — Weihua Fan
(74) *Attorney, Agent, or Firm* — NSIP Law

(57) ABSTRACT

The present disclosure relates to a mutant cell-free DNA isolation kit and a mutant cell-free DNA analysis method using a CRISPR-Cas system and an exonuclease.

12 Claims, 12 Drawing Sheets

Specification includes a Sequence Listing.

[FIG. 1]
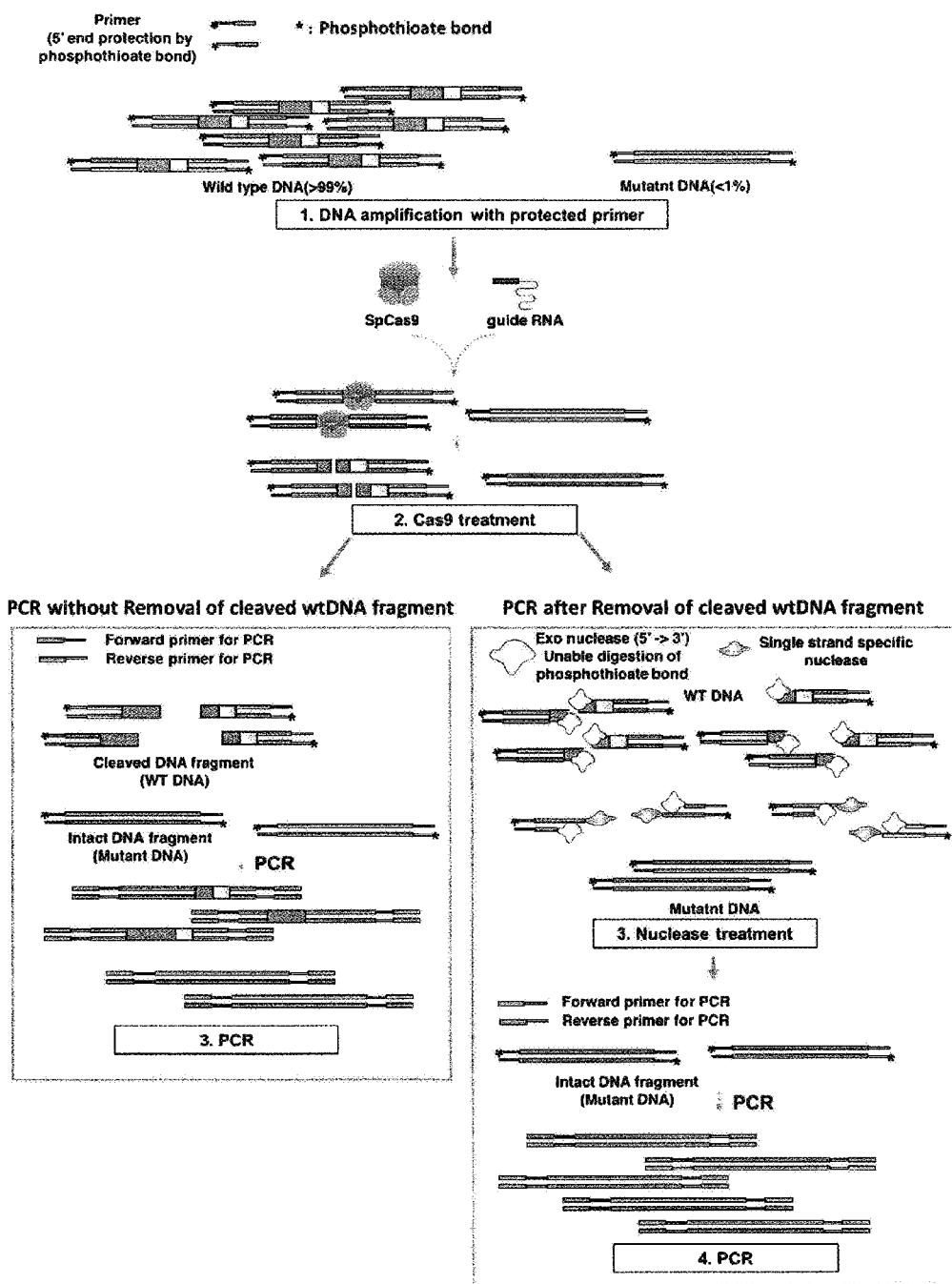

[FIG. 2a]
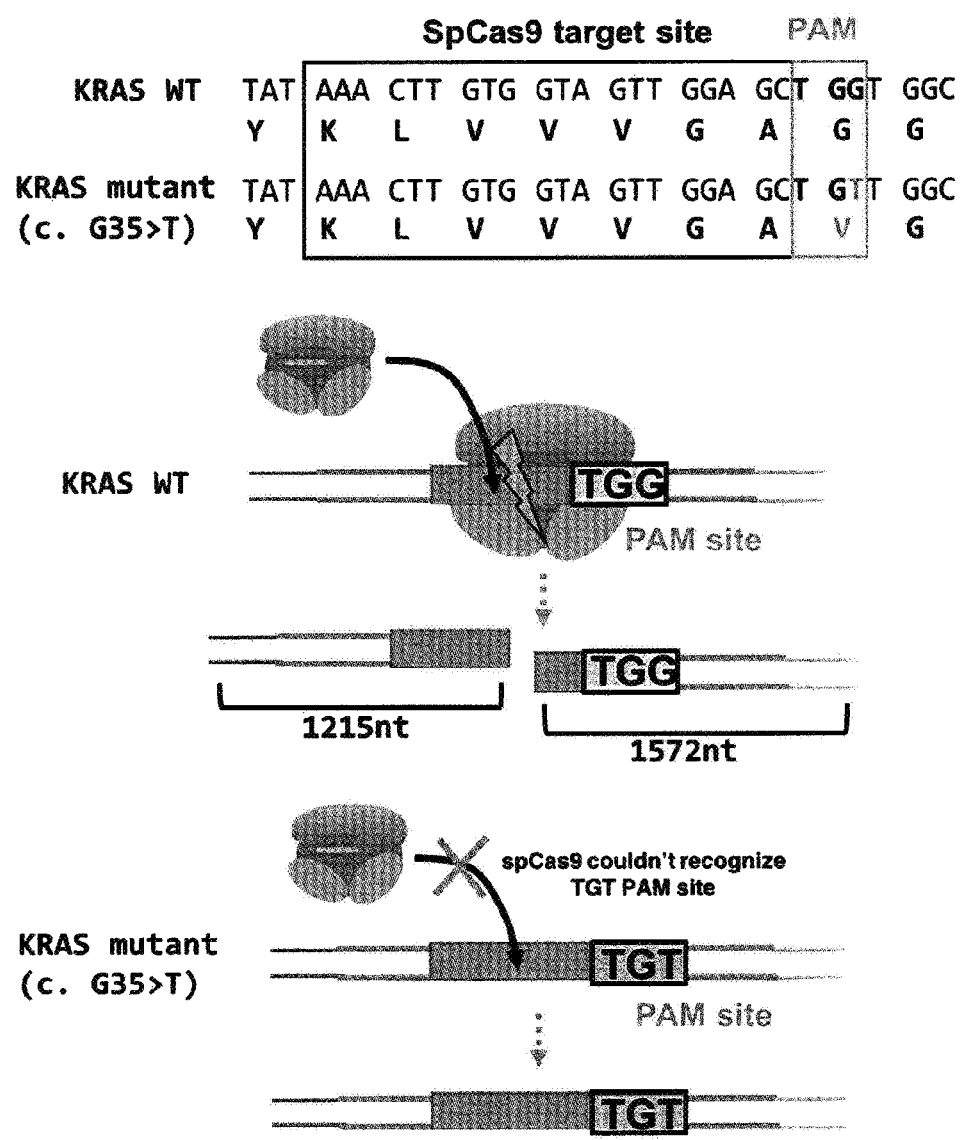

[FIG. 2b]
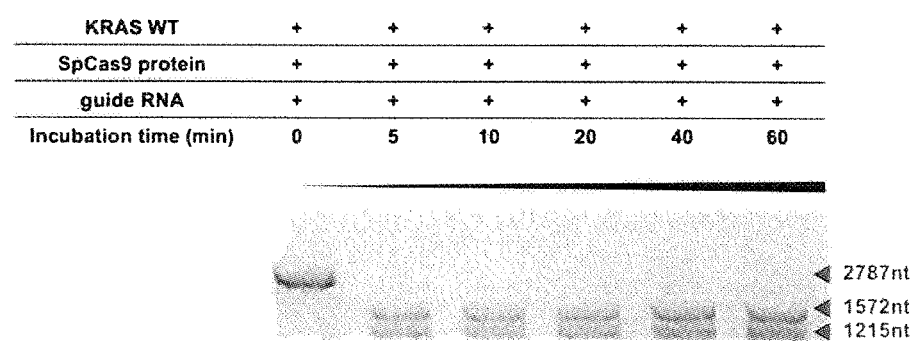
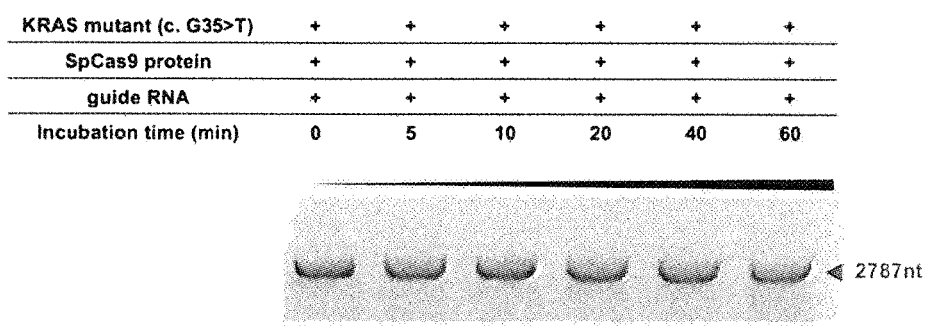

[FIG. 3a]
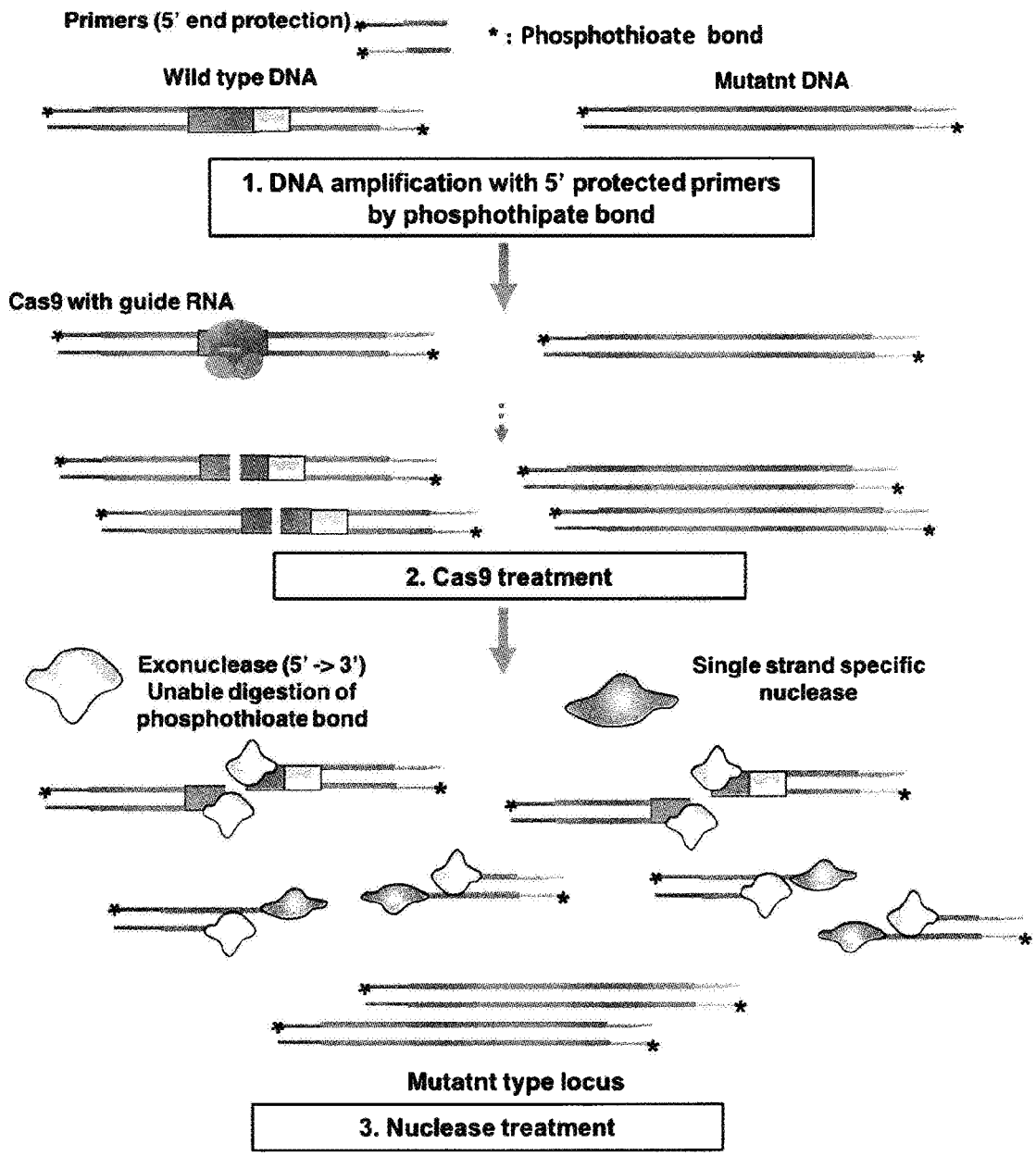

[FIG. 3b]
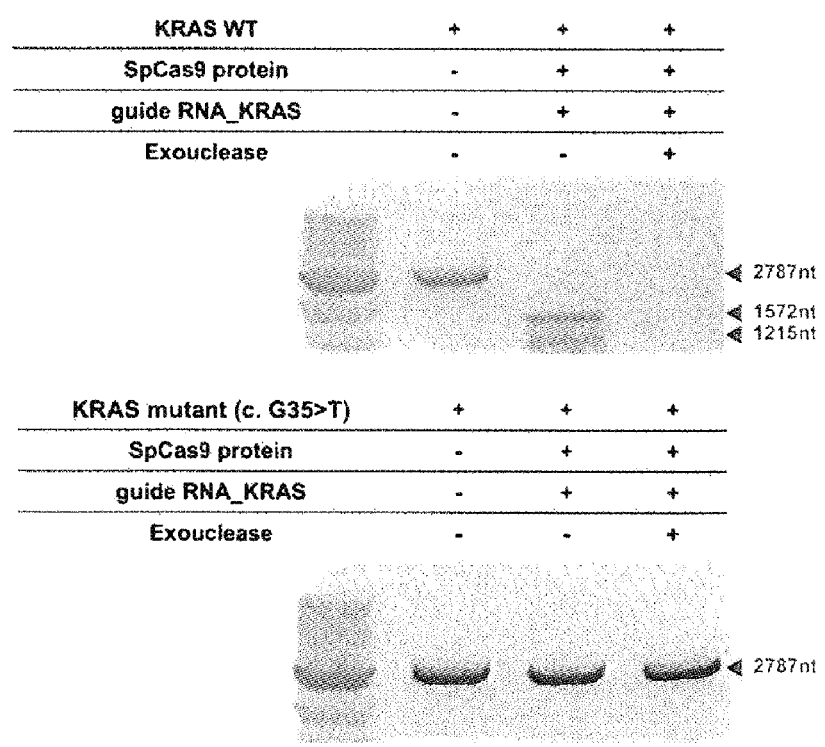

[FIG. 4]
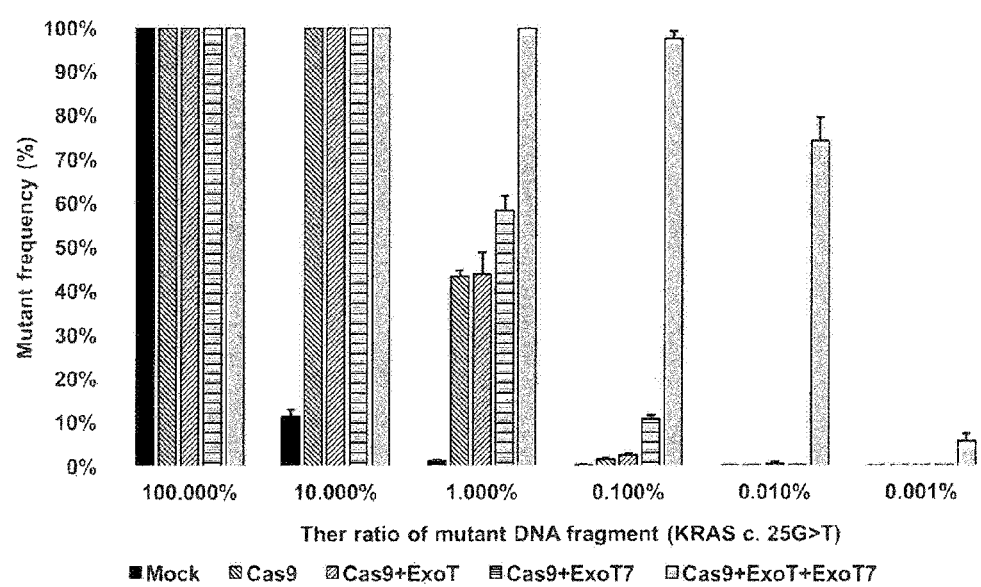

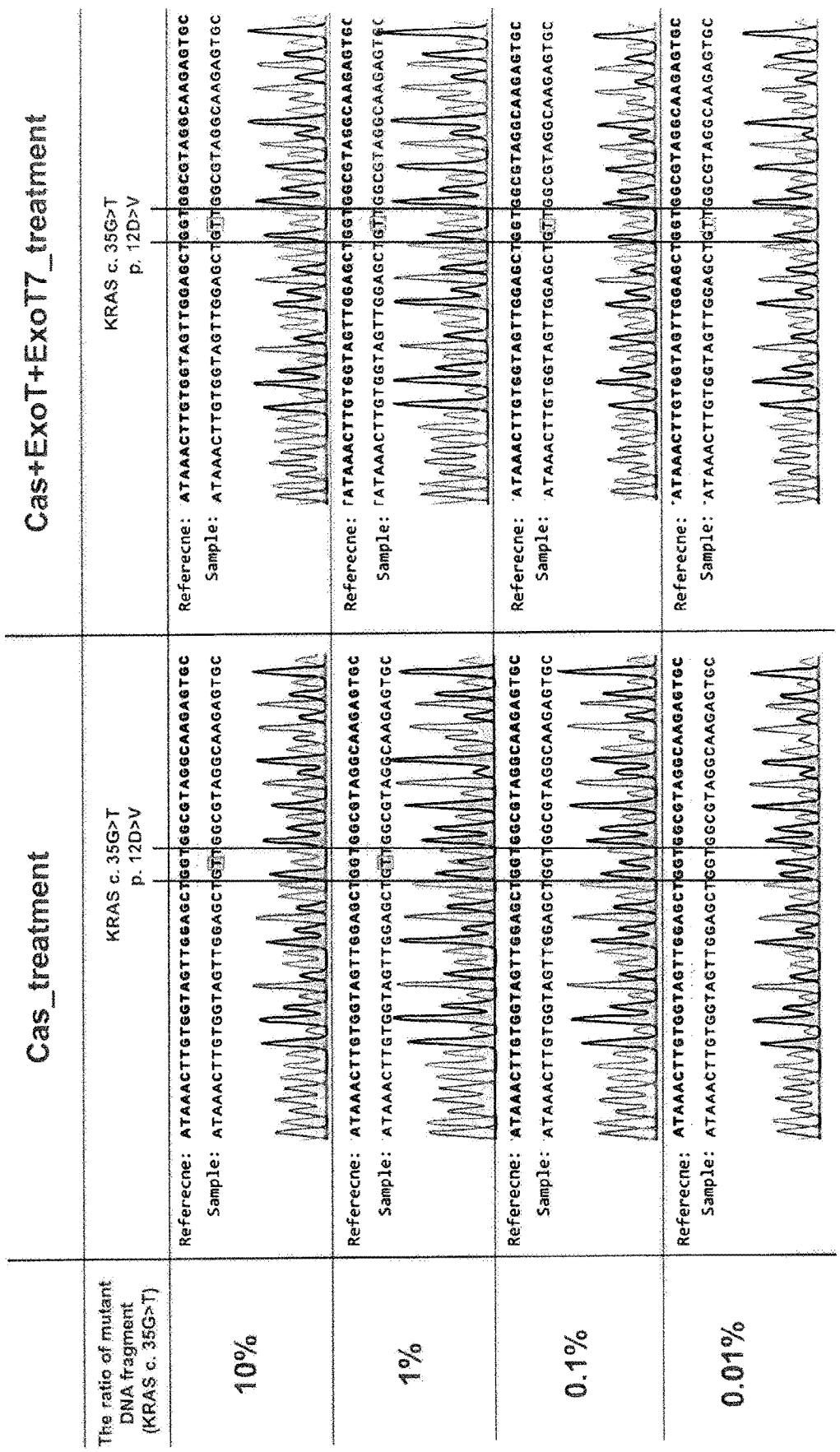
[FIG. 5]

[FIG. 6]
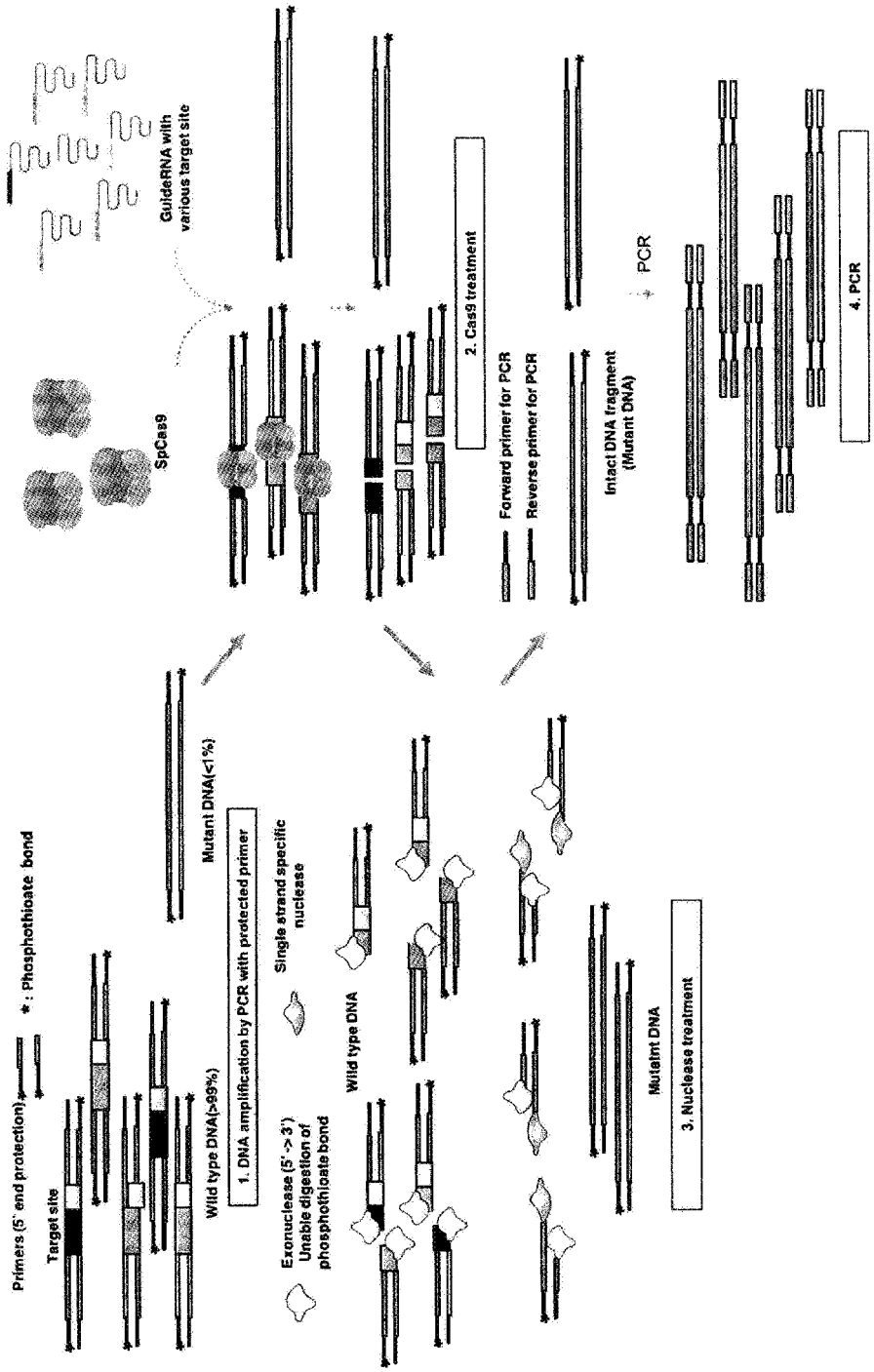

[FIG. 7a]

|  |  | SpCas9 target site | | | | | | PAM | |
|---|---|---|---|---|---|---|---|---|---|
| KRAS WT | TAT | AAA | CTT | GTG | GTA | GTT | GGA | GCT GG | T GGC |
|  | Y | K | L | V | V | V | G | A G | G |
| KRAS mutant | TAT | AAA | CTT | GTG | GTA | GTT | GGA | GCT GT | T GGC |
| (c. G35>T) | Y | K | L | V | V | V | G | A V | G |

| | | SpCas9 target site | | | | | | | |
|---|---|---|---|---|---|---|---|---|---|
| EGFR WT | CCC | GTC | GCT | ATC | AAG | GAA | TTA | AGA | GAA GCA ACA TCT CCG |
|  | P | V | A | I | K | E | L | R | E A T S P |
| EGFR mutant | CCC | GTC | GCT | ATC | AAG | ACA | TCT | CCG | |
| (c. 2235-2249 del) | P | V | A | I | K | T | S | P | |

[FIG. 7b]
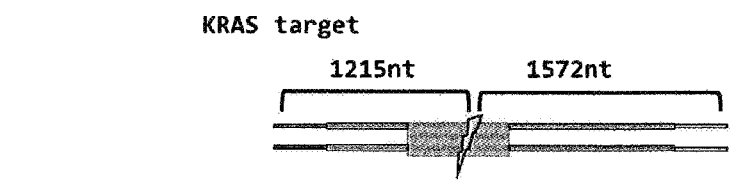
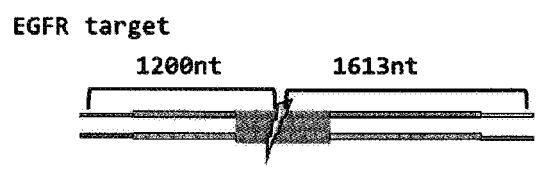
| KRAS, EGFR WT | + | + | + | + | + |
|---|---|---|---|---|---|
| SpCas9 protein | - | + | + | + | + |
| guide RNA_KRAS | - | + | - | + | + |
| guide RNA_EGFR | - | - | + | + | + |
| Exonuclease | - | - | - | - | + |
◀ 2787, 2813nt
◀ 1572, 1613nt
◀ 1215, 1200nt
| KRAS, EGFR mutant | + | + | + | + | + |
|---|---|---|---|---|---|
| SpCas9 protein | - | + | + | + | + |
| guide RNA_KRAS | - | + | - | + | + |
| guide RNA_EGFR | - | - | + | + | + |
| Exonuclease | - | - | - | - | + |
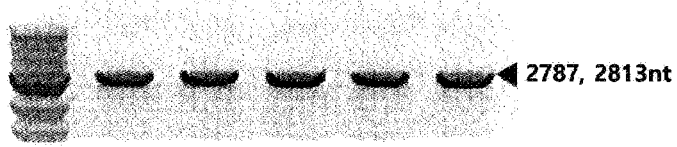
◀ 2787, 2813nt

[FIG. 8]
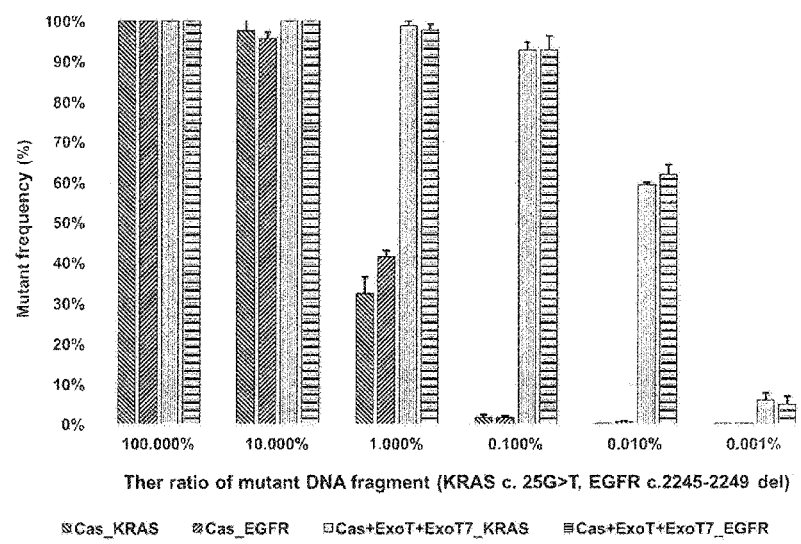

[FIG. 9]
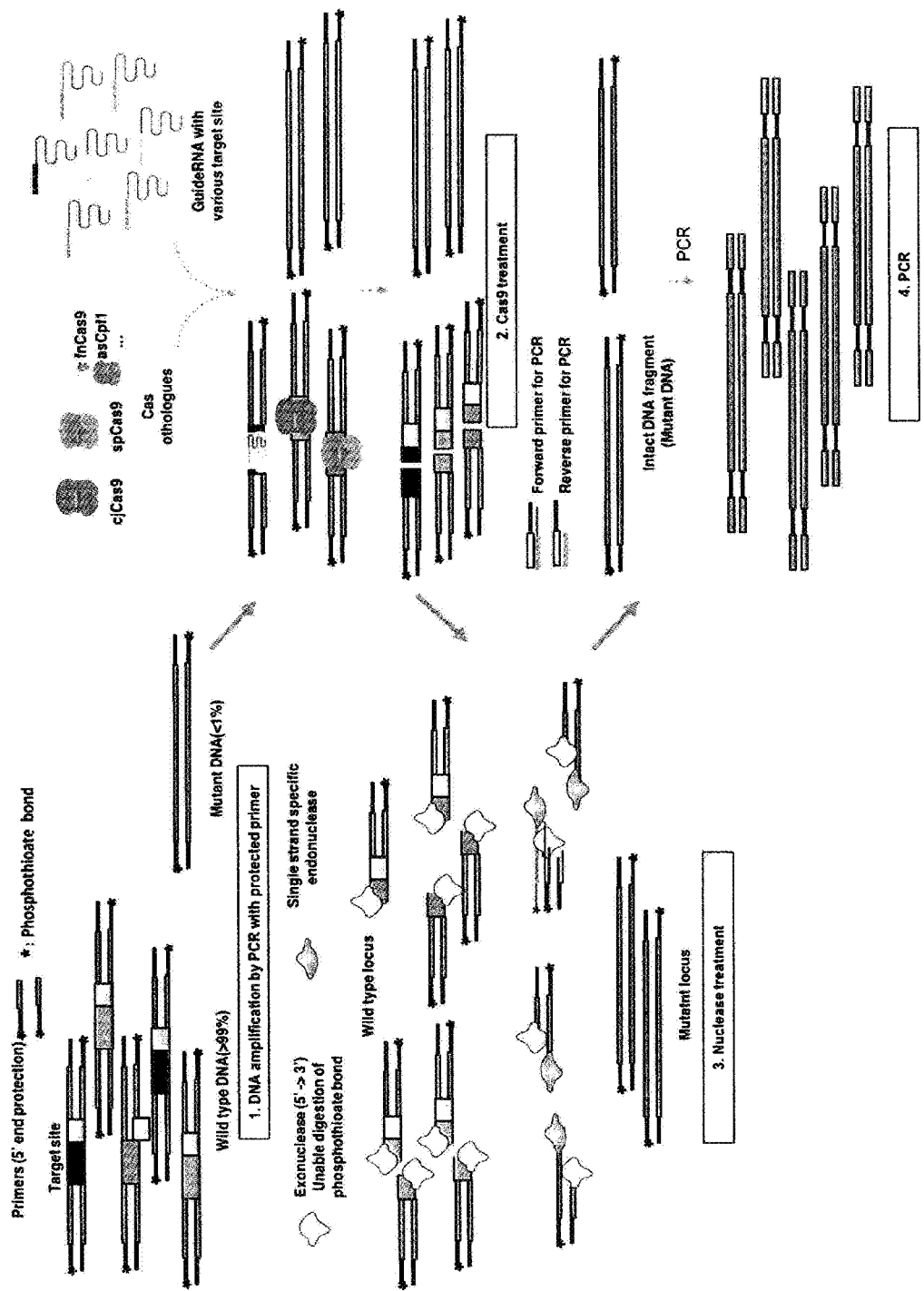

SEQUENCE LISTING

```
<160> NUMBER OF SEQ ID NOS: 19

<210> SEQ ID NO 1
<211> LENGTH: 1383
<212> TYPE: PRT
<213> ORGANISM: Artificial Sequence
<220> FEATURE:
<223> OTHER INFORMATION: spCas9 with 6His

<400> SEQUENCE: 1

Met Gly His His His His His His Ala Glu Leu Pro Gly Ile Arg Pro
1               5                   10                  15

Asp Lys Lys Tyr Ser Ile Gly Leu Asp Ile Gly Thr Asn Ser Val Gly
            20                  25                  30

Trp Ala Val Ile Thr Asp Glu Tyr Lys Val Pro Ser Lys Lys Phe Lys
        35                  40                  45

Val Leu Gly Asn Thr Asp Arg His Ser Ile Lys Lys Asn Leu Ile Gly
    50                  55                  60

Ala Leu Leu Phe Asp Ser Gly Glu Thr Ala Glu Ala Thr Arg Leu Lys
65                  70                  75                  80

Arg Thr Ala Arg Arg Arg Tyr Thr Arg Arg Lys Asn Arg Ile Cys Tyr
                85                  90                  95

Leu Gln Glu Ile Phe Ser Asn Glu Met Ala Lys Val Asp Asp Ser Phe
            100                 105                 110

Phe His Arg Leu Glu Glu Ser Phe Leu Val Glu Glu Asp Lys Lys His
        115                 120                 125

Glu Arg His Pro Ile Phe Gly Asn Ile Val Asp Glu Val Ala Tyr His
    130                 135                 140

Glu Lys Tyr Pro Thr Ile Tyr His Leu Arg Lys Lys Leu Val Asp Ser
145                 150                 155                 160

Thr Asp Lys Ala Asp Leu Arg Leu Ile Tyr Leu Ala Leu Ala His Met
                165                 170                 175

Ile Lys Phe Arg Gly His Phe Leu Ile Glu Gly Asp Leu Asn Pro Asp
            180                 185                 190

Asn Ser Asp Val Asp Lys Leu Phe Ile Gln Leu Val Gln Thr Tyr Asn
        195                 200                 205

Gln Leu Phe Glu Glu Asn Pro Ile Asn Ala Ser Gly Val Asp Ala Lys
    210                 215                 220

Ala Ile Leu Ser Ala Arg Leu Ser Lys Ser Arg Arg Leu Glu Asn Leu
225                 230                 235                 240

Ile Ala Gln Leu Pro Gly Glu Lys Lys Asn Gly Leu Phe Gly Asn Leu
                245                 250                 255

Ile Ala Leu Ser Leu Gly Leu Thr Pro Asn Phe Lys Ser Asn Phe Asp
            260                 265                 270

Leu Ala Glu Asp Ala Lys Leu Gln Leu Ser Lys Asp Thr Tyr Asp Asp
        275                 280                 285
```

-continued

```
Asp Leu Asp Asn Leu Leu Ala Gln Ile Gly Asp Gln Tyr Ala Asp Leu
    290                 295                 300
Phe Leu Ala Ala Lys Asn Leu Ser Asp Ala Ile Leu Leu Ser Asp Ile
305                 310                 315                 320
Leu Arg Val Asn Thr Glu Ile Thr Lys Ala Pro Leu Ser Ala Ser Met
                325                 330                 335
Ile Lys Arg Tyr Asp Glu His His Gln Asp Leu Thr Leu Leu Lys Ala
                340                 345                 350
Leu Val Arg Gln Gln Leu Pro Glu Lys Tyr Lys Glu Ile Phe Phe Asp
            355                 360                 365
Gln Ser Lys Asn Gly Tyr Ala Gly Tyr Ile Asp Gly Gly Ala Ser Gln
    370                 375                 380
Glu Glu Phe Tyr Lys Phe Ile Lys Pro Ile Leu Glu Lys Met Asp Gly
385                 390                 395                 400
Thr Glu Glu Leu Leu Val Lys Leu Asn Arg Glu Asp Leu Leu Arg Lys
                405                 410                 415
Gln Arg Thr Phe Asp Asn Gly Ser Ile Pro His Gln Ile His Leu Gly
            420                 425                 430
Glu Leu His Ala Ile Leu Arg Arg Gln Glu Asp Phe Tyr Pro Phe Leu
        435                 440                 445
Lys Asp Asn Arg Glu Lys Ile Glu Lys Ile Leu Thr Phe Arg Ile Pro
450                 455                 460
Tyr Tyr Val Gly Pro Leu Ala Arg Gly Asn Ser Arg Phe Ala Trp Met
465                 470                 475                 480
Thr Arg Lys Ser Glu Glu Thr Ile Thr Pro Trp Asn Phe Glu Glu Val
                485                 490                 495
Val Asp Lys Gly Ala Ser Ala Gln Ser Phe Ile Glu Arg Met Thr Asn
            500                 505                 510
Phe Asp Lys Asn Leu Pro Asn Glu Lys Val Leu Pro Lys His Ser Leu
        515                 520                 525
Leu Tyr Glu Tyr Phe Thr Val Tyr Asn Glu Leu Thr Lys Val Lys Tyr
    530                 535                 540
Val Thr Glu Gly Met Arg Lys Pro Ala Phe Leu Ser Gly Glu Gln Lys
545                 550                 555                 560
Lys Ala Ile Val Asp Leu Leu Phe Lys Thr Asn Arg Lys Val Thr Val
                565                 570                 575
Lys Gln Leu Lys Glu Asp Tyr Phe Lys Lys Ile Glu Cys Phe Asp Ser
            580                 585                 590
Val Glu Ile Ser Gly Val Glu Asp Arg Phe Asn Ala Ser Leu Gly Thr
        595                 600                 605
Tyr His Asp Leu Leu Lys Ile Ile Lys Asp Lys Asp Phe Leu Asp Asn
    610                 615                 620
Glu Glu Asn Glu Asp Ile Leu Glu Asp Ile Val Leu Thr Leu Thr Leu
625                 630                 635                 640
Phe Glu Asp Arg Glu Met Ile Glu Glu Arg Leu Lys Thr Tyr Ala His
                645                 650                 655
Leu Phe Asp Asp Lys Val Met Lys Gln Leu Lys Arg Arg Arg Tyr Thr
            660                 665                 670
Gly Trp Gly Arg Leu Ser Arg Lys Leu Ile Asn Gly Ile Arg Asp Lys
        675                 680                 685
Gln Ser Gly Lys Thr Ile Leu Asp Phe Leu Lys Ser Asp Gly Phe Ala
    690                 695                 700
```

-continued

```
Asn Arg Asn Phe Met Gln Leu Ile His Asp Asp Ser Leu Thr Phe Lys
705                 710                 715                 720

Glu Asp Ile Gln Lys Ala Gln Val Ser Gly Gln Gly Asp Ser Leu His
            725                 730                 735

Glu His Ile Ala Asn Leu Ala Gly Ser Pro Ala Ile Lys Lys Gly Ile
                740                 745                 750

Leu Gln Thr Val Lys Val Val Asp Glu Leu Val Lys Val Met Gly Arg
            755                 760                 765

His Lys Pro Glu Asn Ile Val Ile Glu Met Ala Arg Glu Asn Gln Thr
        770                 775                 780

Thr Gln Lys Gly Gln Lys Asn Ser Arg Glu Arg Met Lys Arg Ile Glu
785                 790                 795                 800

Glu Gly Ile Lys Glu Leu Gly Ser Gln Ile Leu Lys Glu His Pro Val
                805                 810                 815

Glu Asn Thr Gln Leu Gln Asn Glu Lys Leu Tyr Leu Tyr Tyr Leu Gln
            820                 825                 830

Asn Gly Arg Asp Met Tyr Val Asp Gln Glu Leu Asp Ile Asn Arg Leu
        835                 840                 845

Ser Asp Tyr Asp Val Asp His Ile Val Pro Gln Ser Phe Leu Lys Asp
850                 855                 860

Asp Ser Ile Asp Asn Lys Val Leu Thr Arg Ser Asp Lys Asn Arg Gly
865                 870                 875                 880

Lys Ser Asp Asn Val Pro Ser Glu Glu Val Val Lys Lys Met Lys Asn
                885                 890                 895

Tyr Trp Arg Gln Leu Leu Asn Ala Lys Leu Ile Thr Gln Arg Lys Phe
                900                 905                 910

Asp Asn Leu Thr Lys Ala Glu Arg Gly Gly Leu Ser Glu Leu Asp Lys
            915                 920                 925

Ala Gly Phe Ile Lys Arg Gln Leu Val Glu Thr Arg Gln Ile Thr Lys
930                 935                 940

His Val Ala Gln Ile Leu Asp Ser Arg Met Asn Thr Lys Tyr Asp Glu
945                 950                 955                 960

Asn Asp Lys Leu Ile Arg Glu Val Lys Val Ile Thr Leu Lys Ser Lys
                965                 970                 975

Leu Val Ser Asp Phe Arg Lys Asp Phe Gln Phe Tyr Lys Val Arg Glu
            980                 985                 990

Ile Asn Asn Tyr His His Ala His Asp Ala Tyr Leu Asn Ala Val Val
        995                 1000                1005

Gly Thr Ala Leu Ile Lys Lys Tyr Pro Lys Leu Glu Ser Glu Phe Val
    1010                1015                1020

Tyr Gly Asp Tyr Lys Val Tyr Asp Val Arg Lys Met Ile Ala Lys Ser
1025                1030                1035                1040

Glu Gln Glu Ile Gly Lys Ala Thr Ala Lys Tyr Phe Phe Tyr Ser Asn
                1045                1050                1055

Ile Met Asn Phe Phe Lys Thr Glu Ile Thr Leu Ala Asn Gly Glu Ile
            1060                1065                1070

Arg Lys Arg Pro Leu Ile Glu Thr Asn Gly Glu Thr Gly Glu Ile Val
        1075                1080                1085

Trp Asp Lys Gly Arg Asp Phe Ala Thr Val Arg Lys Val Leu Ser Met
    1090                1095                1100

Pro Gln Val Asn Ile Val Lys Lys Thr Glu Val Gln Thr Gly Gly Phe
1105                1110                1115                1120
```

Ser Lys Glu Ser Ile Leu Pro Lys Arg Asn Ser Asp Lys Leu Ile Ala
        1125                1130                1135

Arg Lys Lys Asp Trp Asp Pro Lys Lys Tyr Gly Gly Phe Asp Ser Pro
        1140                1145                1150

Thr Val Ala Tyr Ser Val Leu Val Val Ala Lys Val Glu Lys Gly Lys
    1155                1160                1165

Ser Lys Lys Leu Lys Ser Val Lys Glu Leu Leu Gly Ile Thr Ile Met
1170                1175                1180

Glu Arg Ser Ser Phe Glu Lys Asn Pro Ile Asp Phe Leu Glu Ala Lys
1185                1190                1195                1200

Gly Tyr Lys Glu Val Lys Lys Asp Leu Ile Ile Lys Leu Pro Lys Tyr
        1205                1210                1215

Ser Leu Phe Glu Leu Glu Asn Gly Arg Lys Arg Met Leu Ala Ser Ala
        1220                1225                1230

Gly Glu Leu Gln Lys Gly Asn Glu Leu Ala Leu Pro Ser Lys Tyr Val
        1235                1240                1245

Asn Phe Leu Tyr Leu Ala Ser His Tyr Glu Lys Leu Lys Gly Ser Pro
    1250                1255                1260

Glu Asp Asn Glu Gln Lys Gln Leu Phe Val Glu Gln His Lys His Tyr
1265                1270                1275                1280

Leu Asp Glu Ile Ile Glu Gln Ile Ser Glu Phe Ser Lys Arg Val Ile
        1285                1290                1295

Leu Ala Asp Ala Asn Leu Asp Lys Val Leu Ser Ala Tyr Asn Lys His
        1300                1305                1310

Arg Asp Lys Pro Ile Arg Glu Gln Ala Glu Asn Ile Ile His Leu Phe
        1315                1320                1325

Thr Leu Thr Asn Leu Gly Ala Pro Ala Ala Phe Lys Tyr Phe Asp Thr
        1330                1335                1340

Thr Ile Asp Arg Lys Arg Tyr Thr Ser Thr Lys Glu Val Leu Asp Ala
1345                1350                1355                1360

Thr Leu Ile His Gln Ser Ile Thr Gly Leu Tyr Glu Thr Arg Ile Asp
        1365                1370                1375

Leu Ser Gln Leu Gly Gly Asp
        1380

<210> SEQ ID NO 2
<211> LENGTH: 96
<212> TYPE: RNA
<213> ORGANISM: Artificial Sequence
<220> FEATURE:
<223> OTHER INFORMATION: KRAS G12V site targeting sgRNA

<400> SEQUENCE: 2
aaacuugugg uaguuggagc guuuuagagc uagaaauagc aaguuaaaau aaggcuaguc    60
cguuaucaac uugaaaaagu ggcaccgagu cggugc                              96

<210> SEQ ID NO 3
<211> LENGTH: 96
<212> TYPE: RNA
<213> ORGANISM: Artificial Sequence
<220> FEATURE:
<223> OTHER INFORMATION: EGFR Del746-750 site targeting sgRNA

<400> SEQUENCE: 3
ucuuaauucc uugauagcga guuuuagagc uagaaauagc aaguuaaaau aaggcuaguc    60
cguuaucaac uugaaaaagu ggcaccgagu cggugc                              96

<210> SEQ ID NO 4
<211> LENGTH: 2786
<212> TYPE: DNA
<213> ORGANISM: Homo sapiens
<220> FEATURE:
<221> NAME/KEY: gene
<222> LOCATION: (1)..(2786)
<223> OTHER INFORMATION: KRAS wt target, human

<400> SEQUENCE: 4

```
tttgtttgtt ttgagatgga gtcttactcc gtcacccaat ctggagtgca gtggcgtgat      60
ctgggctcac tgcaacctct gcctcccggg ttcaagtgat tctccttcct cagcctcccc     120
agtagctagg actacaggag agcgccacca cgcctgatta ttttgtgtat ttttagtaga     180
gagagggttt caccatattg gccaggctgg tcttgaactc ctggcctcag gtgatccacc     240
cgccttggcc tctgaaagtg ctgggattac aggcatgagc cgccgcaccc ggctttctaa     300
tctttatctt ttttgtgca gcggtgatac aggattatgt attgtactga acagttaatt     360
cggagttctc ttggtttta gctttatttt ccccagagat tttttttttt tttttttttt     420
ttgagacgga gtcttgctct atcgccaggc tggagtgcag tggcgccatc tcggctcatt     480
gcaacctcgg actcctattt tccccagaga tatttcacac attaaaatgt cgtcaaatat     540
tgttcttctt tgcctcagtg tttaaatttt tatttcccca tgcacaaatc cagctttatt     600
tgacactcat tctctcaact ctcatctgat tcttactgtt aatatttatc caagagaact     660
actgccatga tgctttaaaa gttttctgt agctgttgca tattgacttc taacacttag     720
aggtggggt ccactaggaa aactgtaaca ataagagtgg atagctgt cagcaacttt     780
tgtgaggtg tgctacaggg tgtagagcac tgtgaagtct ctacatgagt gaagtcatga     840
tatgatcctt tgagagcctt tagccgccgc agaacagcag tctggctatt tagatagaac     900
aacttgattt taagataaaa gaactgtcta tgtagcattt atgcattttt cttaagcgtc     960
gatggaggag tttgtaaatg aagtacagtt cattacgata cacgtctgca gtcaactgga    1020
attttcatga ttgaattttg taaggtattt tgaaataatt tttcatataa aggtgagttt    1080
gtattaaaag gtactggtgg agtatttgat agtgtattaa ccttatgtgt gacatgttct    1140
aatatagtca cattttcatt atttttatta taaggcctgc tgaaaatgac tgaatataaa    1200
cttgtggtag ttggagctgg tggcgtaggc aagagtgcct tgacgataca gctaattcag    1260
aatcattttg tggacgaata tgatccaaca atagaggtaa atcttgtttt aatatgcata    1320
ttactggtgc aggaccattc tttgatacag ataaaggttt ctctgaccat ttcatgagt    1380
acttattaca agataattat gctgaaagtt aagttatctg aaatgtacct tgggtttcaa    1440
gttatatgta accattaata tgggaacttt actttccttg ggagtatgtc agggtccatg    1500
atgttcactc tctgtgcatt tgattggaa gtgtatttca gagtttcgtg agagggtaga    1560
aatttgtatc ctatctggac ctaaaagaca atctttttat tgtaacttt attttatgg    1620
gtttcttggt attgtgacat catatgtaaa ggttagattt aattgtacta gtgaaatata    1680
attgttgat ggttgattt tttaaacttc atcagcagta ttttcctatc ttcttctcaa    1740
cattagagaa cctacaacta ccggataaat tttacaaaat gaattatttg cctaaggtgt    1800
ggtttatata aaggtactat taccaacttt acctttgctt tgttgtcatt tttaaattta    1860
ctcaaggaaa tactaggatt taaaaaaaaa ttccttgagt aaatttaaat tgttatcatg    1920
tttttgagga ttattttcag atttttttag tttaatgaaa atttaccaaa gtaaagacca    1980
```

```
gcagcagaat gataagtaaa gacctgtaag acaccttgaa ggtcatggag tagaacttcc    2040
atcccaagca gatgaggatt tatttaatct caaagacctc caggagggga cattccccaa    2100
ctgtccttgt taactcattt tcagaacata tttattagca tattttacat gtaatttgga    2160
tcttcatgtt aaatttaaca tcagtggaga tggaaaataa gcatatcgcc ttgtctttga    2220
aatagcccta tattgttaga ttgtttctta ggcttcttta ccctgggtta agcagtccta    2280
atactttagc atttattcta catctagtgt actaatttaa aaaaatcagt tctgaaaaat    2340
ttctaagaac tttcttcaag ttccaagctg tgaaatctag aacaggtcaa agtgccttat    2400
taacgtactg tactgtgtag tgtcttgaag agacactttg cgctgaggca agttctgagg    2460
gcattgggtg gccttgggaa gatatttatg cagtttagaa cctggagaat tgattagata    2520
actaatcata aggaaacgtc acatattttt ggtactataa aaaagtggag aaataatgcc    2580
tatttgcaaa gatttgattt aaacatagaa acaactttat ttggcttcca attttaagaa    2640
tttacagcag taaaggggaa cagtctaatt gaagtagact gcctatgcaa tagtctctgt    2700
atatttactt ttgacaagtt aattcaatgt gtactatagt tttgtttctt tgaagaggtt    2760
tgaatagtgc acccatttta atctgt                                        2786
```

```
<210> SEQ ID NO 5
<211> LENGTH: 186
<212> TYPE: PRT
<213> ORGANISM: Homo sapiens
<220> FEATURE:
<221> NAME/KEY: PEPTIDE
<222> LOCATION: (1)..(186)
<223> OTHER INFORMATION: wt KRAS Amino Acids

<400> SEQUENCE: 5

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys
            180                 185

<210> SEQ ID NO 6
<211> LENGTH: 2787
```

```
<212> TYPE: DNA
<213> ORGANISM: Homo sapiens
<220> FEATURE:
<221> NAME/KEY: gene
<222> LOCATION: (1)..(2787)
<223> OTHER INFORMATION: KRAS MUTANT G12V target , HUMAN

<400> SEQUENCE: 6
gtttgtttgt tttgagatgg agtcttactc cgtcacccaa tctggagtgc agtggcgtga      60
tctgggctca ctgcaacctc tgcctcccgg gttcaagtga ttctccttcc tcagcctccc     120
cagtagctag gactacagga gagcgccacc acgcctgatt aattttttgta ttttttagtag    180
agagagggtt tcaccatatt ggccaggctg gtcttgaact cctggcctca ggtgatccac     240
ccgccttggc ctctgaaagt gctgggatta caggcatgag ccgccgcacc cggctttcta     300
atctttatct ttttttgtgc agcggtgata caggattatg tattgtactg aacagttaat     360
tcggagttct cttggttttt agctttattt tccccagaga tttttttttt tttttttttt     420
tttgagacgg agtcttgctc tatcgccagg ctggagtgca gtggcgccat ctcggctcat     480
tgcaacctcg gactcctatt tccccagag atatttcaca cattaaaatg tcgtcaaata      540
ttgttcttct ttgcctcagt gtttaaattt ttatttcccc atgacacaat ccagctttat     600
ttgacactca ttctctcaac tctcatctga ttcttactgt taatatttat ccaagagaac     660
tactgccatg atgctttaaa agttttttctg tagctgttgc atattgactt ctaacactta    720
gaggtgggg tccactagga aaactgtaac aataagagtg gagatagctg tcagcaactt      780
ttgtgagggt gtgctacagg gtgtagagca ctgtgaagtc tctacatgag tgaagtcatg     840
atatgatcct ttgagagcct ttagccgccg cagaacagca gtctggctat ttagatagaa    900
caacttgatt ttaagataaa agaactgtct atgtagcatt tatgcatttt tcttaagcgt     960
cgatggagga gtttgtaaat gaagtacagt tcattacgat acacgtctgc agtcaactgg    1020
aattttcatg attgaatttt gtaaggtatt ttgaaataat ttttcatata aggtgagtt      1080
tgtattaaaa ggtactggtg gagtatttga tagtgtatta accttatgtg tgacatgttc    1140
taatatagtc acatttttcat tatttttatt ataaggcctg ctgaaaatga ctgaatataa   1200
acttgtggta gttggagctg ttggcgtagg caagagtgcc ttgacgatac agctaattca    1260
gaatcatttt gtggacgaat atgatccaac aatagaggta atcttgtttt taatatgcat    1320
attactggtg caggaccatt ctttgataca gataaaggtt tctctgacca ttttcatgag    1380
tacttattac aagataatta tgctgaaagt taagttatct gaaatgtacc ttgggtttca    1440
agttatatgt aaccattaat atgggaactt tactttcctt gggagtatgt cagggtccat    1500
gatgttcact ctctgtgcat tttgattgga agtgtatttc agagtttcgt gagagggtag    1560
aaatttgtat cctatctgga cctaaaagac aatcttttta ttgtaacttt tattttatg     1620
ggtttcttgg tattgtgaca tcatatgtaa aggttagatt taattgtact agtgaaatat    1680
aattgtttga tggttgattt ttttaaactt catcagcagt attttcctat cttcttctca    1740
acattagaga acctacaact accggataaa ttttacaaaa tgaattattt gcctaaggtg    1800
tggtttatat aaaggtacta ttaccaactt tacctttgct ttgttgtcat ttttaaattt    1860
actcaaggaa atactaggat ttaaaaaaaa attccttgag taaatttaaa ttgttatcat    1920
gttttttgagg attattttca gatttttttta gtttaatgaa aatttaccaa agtaaagacc   1980
agcagcagaa tgataagtaa agacctgtaa gacaccttga aggtcatgga gtagaacttc    2040
catcccaagc agatgaggat ttatttaatc tcaaagacct ccaggagggg acattcccca    2100
```

```
actgtccttg ttaactcatt ttcagaacat atttattagc atattttaca tgtaatttgg    2160
atcttcatgt taaatttaac atcagtggag atggaaaata agcatatcgc cttgtctttg    2220
aaatagccct atattgttag attgtttctt aggcttcttt accctgggtt aagcagtcct    2280
aatactttag catttattct acatctagtg tactaattta aaaaaatcag ttctgaaaaa    2340
tttctaagaa ctttcttcaa gttccaagct gtgaaatcta gaacaggtca aagtgcctta    2400
ttaacgtact gtactgtgta gtgtcttgaa gagacacttt gcgctgaggc aagttctgag    2460
ggcattgggt ggccttggga agatatttat gcagtttaga acctggagaa ttgattagat    2520
aactaatcat aaggaaacgt cacatatttt tggtactata aaaaagtgga gaaataatgc    2580
ctatttgcaa agatttgatt taaacataga aacaacttta tttggcttcc aattttaaga    2640
atttacagca gtaaagggga acagtctaat tgaagtagac tgcctatgca atagtctctg    2700
tatatttact tttgacaagt taattcaatg tgtactatag ttttgtttct ttgaagaggt    2760
ttgaatagtg cacccatttt aatctgt                                       2787
```

<210> SEQ ID NO 7
<211> LENGTH: 186
<212> TYPE: PRT
<213> ORGANISM: Homo sapiens
<220> FEATURE:
<221> NAME/KEY: PEPTIDE
<222> LOCATION: (1)..(186)
<223> OTHER INFORMATION: mutant KRAS Amino Acids
<400> SEQUENCE: 7

```
Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys
            180                 185
```

<210> SEQ ID NO 8
<211> LENGTH: 23
<212> TYPE: DNA
<213> ORGANISM: Artificial Sequence
<220> FEATURE:
<223> OTHER INFORMATION: KRAS target site including PAM

<400> SEQUENCE: 8
aaacttgtgg tagttggagc tgg                                      23

<210> SEQ ID NO 9
<211> LENGTH: 2813
<212> TYPE: DNA
<213> ORGANISM: Homo sapiens
<220> FEATURE:
<221> NAME/KEY: gene
<222> LOCATION: (1)..(2813)
<223> OTHER INFORMATION: EGFR wt target sequence, human

<400> SEQUENCE: 9

| | |
|---|---|
| ctcataagca taagcgcgtg tgatgtgccc caaccaaacg accgccatgc acaacttccc | 60 |
| taccggagtt ttcaatccag ttaataggcg tggaaacaga catagaaatt gtgtttgttg | 120 |
| aaaggtagct gttcagttaa agaacacctg tatcagagcc tgtgtttcta ccaacttctg | 180 |
| tcaagctctg tagagaaggc gtacatttgt ccttccaaat gagctggcaa gtgccgtgtc | 240 |
| ctggcaccca agcccatgcc gtggctgctg gtcccctgc tgggccatgt ctggcactgc | 300 |
| tttccagcat ggtgagggct gaggtgaccc ttgtctctgt gttcttgtcc ccccagctt | 360 |
| gtggagcctc ttacacccag tggagaagct cccaaccaag ctctcttgag gatcttgaag | 420 |
| gaaactgaat tcaaaaagat caaagtgctg ggctccggtg cgttcggcac ggtgtataag | 480 |
| gtaaggtccc tggcacaggc tctgggctg gccgcaggg cctctcatgg tctggtgggg | 540 |
| agcccagagt ccttgcaagc tgtatatttc catcatctac tttactcttt gtttcactga | 600 |
| gtgtttggga aactccagtg ttttttccaa gttattgaga ggaaatcttt tataaccaca | 660 |
| gtaatcagtg gtcctgtgag accaattcac agaccaaagg cattttatg aaagggccca | 720 |
| ttgaccttgc catgggtgc agcacagggc gggaggaggg ccgcctctca ccgcacggca | 780 |
| tcagaatgca gcccagctga atgggctca tcttcgtttg cttcttctag atcctctttg | 840 |
| catgaaatct gatttcagtt aggcctagac gcagcatcat taaattctgg atgaaatgat | 900 |
| ccacacggac tttataacag gctttacaag cttgagattc ttttatctaa ataatcagtg | 960 |
| tgattcgtgg agcccaacag ctgcagggct gcggggcgt cacagccccc agcaatatca | 1020 |
| gccttaggtg cggctccaca gccccagtgt ccctcacctt cggggtgcat cgctggtaac | 1080 |
| atccacccag atcactgggc agcatgtggc accatctcac aattgccagt taacgtcttc | 1140 |
| cttctctctc tgtcataggg actctggatc ccagaaggtg agaaagttaa aattcccgtc | 1200 |
| gctatcaagg aattaagaga agcaacatct ccgaaagcca acaaggaaat cctcgatgtg | 1260 |
| agtttctgct ttgctgtgtg ggggtccatg gctctgaacc tcaggcccac cttttctcat | 1320 |
| gtctggcagc tgctctgctc tagaccctgc tcatctccac atcctaaatg ttcacttct | 1380 |
| atgtctttcc ctttctagct ctagtgggta taactccctc cccttagaga cagcactggc | 1440 |
| ctctcccatg ctggtatcca ccccaaaagg ctggaaacag gcaattactg gcatctaccc | 1500 |
| agcactagtt tcttgacacg catgatgagt gagtgctctt ggtgagcctg gagcatgggt | 1560 |
| attgttttg gtattttttg gatgaagaaa tggaggcata agaaaattgg ctgacccctta | 1620 |
| tatggctggg atagggttta agcccccttgt tatttctgac tctgaaactt gcattcaatt | 1680 |
| cactccacca agttatctca tctttgaaat ggcttttttt aaaggtgcct agaatatgat | 1740 |
| ggcgtgcagt ctataaactg ttgcccacct tctgtacttt ctctcagaat aattcacatt | 1800 |
| cttctccagt gtctgttgat tgttactttg tggaataagt tcttggaaaa ttccacaaga | 1860 |

-continued

```
ttattgttat cttcttacta ccaattctat tgaactttct ccaccttctc tgggccttcc    1920
ccagccagtg gtgggaagat gctggctgga gtctgacaga gcctcttcta cactggcctg    1980
ggcttgctgt gagttggtgg aaacctttgc tcttgtccca acacagagca agtgaaagag    2040
gaggtcaagg ggctcaggca gcggactagg gaagcagaat cgaggaaaag gaaaatggc     2100 tgacttatta cctcaaaact ctagagaatt tagttgatct tacagccaag aaggacaaaa    2160
gccagagagt aatatcctcc gcctcatgtc taacccacag aatacatagc aagtaaagag    2220
aacatgggcc tttataaaaa tgtcttaaga tacaattttt taattggagg aaatctacag    2280
tttaattttc tctgggcagc ttttcttcct tttattatag taggggaaat cccatgttga    2340
tatacttcta aatgaaagat gatgaattga tataatacaa taaaaaatct gtaaaattga    2400
tgatatactt atcaagaaaa attagctttc atttttaacgg tttacaaatt gagtcaagtc    2460
ctagtaacaa aatgttaagt ctattaacat aaccacaaga aatacaggaa gacgggcaat    2520
ctgtgaagcc tttcacttac aatctctggc ccctcacctg tgctgtgtag gaaaatcttt    2580
gtgcacaatt tgcttcctta attcattttt tattcattca acacattcta ataaattata    2640
caaaatcatg ttgaaatgtg aatttcagtg gtatttataa atgcagtgtg aggagggttt    2700
ggatgtattc taagacaata gttgtgcttt gggaaggaag cagtgttcac tgaaaagtgc    2760
ccccaggacc ttttaattgg aggaaatatg cttctgtgga gttggaaatg ggg           2813
```

<210> SEQ ID NO 10
<211> LENGTH: 1210
<212> TYPE: PRT
<213> ORGANISM: Homo sapiens

<400> SEQUENCE: 10

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205
```

-continued

```
Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620
```

-continued

```
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
            645                 650                 655
Leu Leu Val Val Ala Leu Gly Ile Gly Leu Phe Met Arg Arg His
        660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
        690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
        850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
        930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe Phe
    1010                1015                1020
Ser Ser Pro Ser Thr Ser Arg Thr Pro Leu Leu Ser Ser Leu Ser Ala
1025                1030                1035                1040
```

```
Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
        1140                1145                1150

Ser Pro Ala His Trp Ala Gln Lys Gly Ser His Gln Ile Ser Leu Asp
    1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

<210> SEQ ID NO 11
<211> LENGTH: 2798
<212> TYPE: DNA
<213> ORGANISM: Homo sapiens
<220> FEATURE:
<221> NAME/KEY: gene
<222> LOCATION: (1)..(2798)
<223> OTHER INFORMATION: EGFR Deletion mutant. 746-750

<400> SEQUENCE: 11
ctcataagca taagcgcgtg tgatgtgccc caaccaaacg accgccatgc acaacttccc      60
taccggagtt ttcaatccag ttaataggcg tggaaacaga catagaaatt gtgtttgttg     120
aaaggtagct gttcagttaa agaacacctg tatcagagcc tgtgtttcta ccaacttctg     180
tcaagctctg tagagaaggc gtacatttgt ccttccaaat gagctggcaa gtgccgtgtc     240
ctggcaccca agcccatgcc gtggctgctg gtccccctgc tgggccatgt ctggcactgc     300
tttccagcat ggtgagggct gaggtgaccc ttgtctctgt gttcttgtcc cccccagctt     360
gtggagcctc ttacacccag tggagaagct cccaaccaag ctctcttgag gatcttgaag     420
gaaactgaat tcaaaaagat caaagtgctg gctccggtg cgttcggcac ggtgtataag     480
gtaaggtccc tggcacaggc ctctgggctg gccgcaggg cctctcatgg tctggtgggg     540
agcccagagt ccttgcaagc tgtatatttc catcatctac tttactcttt gtttcactga     600
gtgtttggga aactccagtg ttttttcccaa gttattgaga ggaaatcttt tataaccaca     660
gtaatcagtg gtcctgtgag accaattcac agaccaaagg catttttatg aaaggggcca     720
ttgaccttgc catggggtgc agcacagggc gggaggaggg ccgcctctca ccgcacggca     780
tcagaatgca gcccagctga atgggctca tcttcgtttg cttcttctag atcctctttg      840
catgaaatct gatttcagtt aggcctagac gcagcatcat taaattctgg atgaaatgat     900
ccacacggac tttataacag gctttacaag cttgagattc ttttatctaa ataatcagtg     960
tgattcgtgg agcccaacag ctgcagggct gcggggcgt cacagccccc agcaatatca     1020
```

-continued

```
gccttaggtg cggctccaca gccccagtgt ccctcacctt cggggtgcat cgctggtaac      1080
atccacccag atcactgggc agcatgtggc accatctcac aattgccagt taacgtcttc      1140
cttctctctc tgtcataggg actctggatc ccagaaggtg agaaagttaa aattcccgtc      1200
gctatcaaga catctccgaa agccaacaag gaaatcctcg atgtgagttt ctgctttgct      1260 gtgtggggt ccatggctct gaacctcagg cccacctttt ctcatgtctg gcagctgctc       1320
tgctctagac cctgctcatc tccacatcct aaatgttcac tttctatgtc tttcccttc      1380 tagctctagt gggtataact ccctcccctt agagacagca ctggcctctc ccatgctggt      1440
atccacccca aaaggctgga acaggcaat tactggcatc tacccagcac tagtttcttg       1500
acacgcatga tgagtgagtg ctcttggtga gcctggagca tgggtattgt ttttggtatt      1560
ttttggatga agaaatggag gcataaagaa attggctgac ccttatatgg ctgggatagg      1620
gtttaagccc cttgttattt ctgactctga aacttgcatt caattcactc caccaagtta      1680
tctcatcttt gaaatggctt ttttaaagg tgcctagaat atgatggcgt gcagtctata      1740
aactgttgcc caccttctgt actttctctc agaataattc acattcttct ccagtgtctg      1800
ttgattgtta ctttgtggaa taagttcttg gaaaattcca caagattatt gttatcttct      1860
tactaccaat tctattgaac tttctccacc ttctctgggc cttccccagc cagtggtggg      1920
aagatgctgg ctggagtctg acagagcctc ttctacactg gcctgggctt gctgtgagtt      1980
ggtggaaacc tttgctcttg tcccaacaca gagcaagtga agaggaggt caaggggctc       2040 aggcagcgga ctagggaagc agaatcgagg aaaaggaaaa atggctgact tattacctca      2100
aaactctaga gaatttagtt gatcttacag ccaagaagga caaaagccag agagtaatat      2160
cctccgcctc atgtctaacc cacagaatac atagcaagta aagagaacat gggcctttat      2220
aaaaatgtct taagatacaa ttttttaatt ggaggaaatc tacagtttaa ttttctctgg      2280
gcagcttttc ttcctttat tatagtaggg gaaatcccat gttgatatac ttctaaatga       2340
aagatgatga attgatataa tacaataaaa aatctgtaaa attgatgata tacttatcaa      2400
gaaaaattag ctttcatttt aacggtttac aaattgagtc aagtcctagt aacaaaatgt      2460
taagtctatt aacataacca caagaaatac aggaagacgg gcaatctgtg aagcctttca      2520
cttacaatct ctggcccctc acctgtgctg tgtaggaaaa tctttgtgca caatttgctt      2580
ccttaattca ttttttattc attcaacaca ttctaataaa ttatacaaaa tcatgttgaa      2640
atgtgaattt cagtggtatt tataaatgca gtgtgaggag ggtttggatg tattctaaga      2700
caatagttgt gctttgggaa ggaagcagtg ttcactgaaa agtgccccca ggacctttta      2760
attggaggaa atatgcttct gtggagttgg aaatgggg                             2798
```

<210> SEQ ID NO 12
<211> LENGTH: 1140
<212> TYPE: PRT
<213> ORGANISM: Homo sapiens
<220> FEATURE:
<221> NAME/KEY: PEPTIDE
<222> LOCATION: (1)..(1140)
<223> OTHER INFORMATION: EGFR Deletion mutant Amino Acids

<400> SEQUENCE: 12

```
Glu Ile Thr Tyr Val Gln Arg Asn Tyr Asp Leu Ser Phe Leu Lys Thr
1               5                   10                  15

Ile Gln Glu Val Ala Gly Tyr Val Leu Ile Ala Leu Asn Thr Val Glu
            20                  25                  30
```

```
Arg Ile Pro Leu Glu Asn Leu Gln Ile Ile Arg Gly Asn Met Tyr Tyr
         35                  40                  45

Glu Asn Ser Tyr Ala Leu Ala Val Leu Ser Asn Tyr Asp Ala Asn Lys
 50                  55                  60

Thr Gly Leu Lys Glu Leu Pro Met Arg Asn Leu Gln Glu Ile Leu His
 65                  70                  75                  80

Gly Ala Val Arg Phe Ser Asn Asn Pro Ala Leu Cys Asn Val Glu Ser
                 85                  90                  95

Ile Gln Trp Arg Asp Ile Val Ser Ser Asp Phe Leu Ser Asn Met Ser
             100                 105                 110

Met Asp Phe Gln Asn His Leu Gly Ser Cys Gln Lys Cys Asp Pro Ser
         115                 120                 125

Cys Pro Asn Gly Ser Cys Trp Gly Ala Gly Glu Glu Asn Cys Gln Lys
     130                 135                 140

Leu Thr Lys Ile Ile Cys Ala Gln Gln Cys Ser Gly Arg Cys Arg Gly
145                 150                 155                 160

Lys Ser Pro Ser Asp Cys Cys His Asn Gln Cys Ala Ala Gly Cys Thr
                 165                 170                 175

Gly Pro Arg Glu Ser Asp Cys Leu Val Cys Arg Lys Phe Arg Asp Glu
             180                 185                 190

Ala Thr Cys Lys Asp Thr Cys Pro Pro Leu Met Leu Tyr Asn Pro Thr
         195                 200                 205

Thr Tyr Gln Met Asp Val Asn Pro Glu Gly Lys Tyr Ser Phe Gly Ala
     210                 215                 220

Thr Cys Val Lys Lys Cys Pro Arg Asn Tyr Val Val Thr Asp His Gly
225                 230                 235                 240

Ser Cys Val Arg Ala Cys Gly Ala Asp Ser Tyr Glu Met Glu Glu Asp
                 245                 250                 255

Gly Val Arg Lys Cys Lys Lys Cys Glu Gly Pro Cys Arg Lys Val Cys
             260                 265                 270

Asn Gly Ile Gly Ile Gly Glu Phe Lys Asp Ser Leu Ser Ile Asn Ala
         275                 280                 285

Thr Asn Ile Lys His Phe Lys Asn Cys Thr Ser Ile Ser Gly Asp Leu
     290                 295                 300

His Ile Leu Pro Val Ala Phe Arg Gly Asp Ser Phe Thr His Thr Pro
305                 310                 315                 320

Pro Leu Asp Pro Gln Glu Leu Asp Ile Leu Lys Thr Val Lys Glu Ile
                 325                 330                 335

Thr Gly Phe Leu Leu Ile Gln Ala Trp Pro Glu Asn Arg Thr Asp Leu
             340                 345                 350

His Ala Phe Glu Asn Leu Glu Ile Ile Arg Gly Arg Thr Lys Gln His
         355                 360                 365

Gly Gln Phe Ser Leu Ala Val Val Ser Leu Asn Ile Thr Ser Leu Gly
     370                 375                 380

Leu Arg Ser Leu Lys Glu Ile Ser Asp Gly Asp Val Ile Ile Ser Gly
385                 390                 395                 400

Asn Lys Asn Leu Cys Tyr Ala Asn Thr Ile Asn Trp Lys Lys Leu Phe
                 405                 410                 415

Gly Thr Ser Gly Gln Lys Thr Lys Ile Ile Ser Asn Arg Gly Glu Asn
             420                 425                 430

Ser Cys Lys Ala Thr Gly Gln Val Cys His Ala Leu Cys Ser Pro Glu
         435                 440                 445
```

```
Gly Cys Trp Gly Pro Glu Pro Arg Asp Cys Val Ser Cys Arg Asn Val
    450                 455                 460

Ser Arg Gly Arg Glu Cys Val Asp Lys Cys Asn Leu Leu Glu Gly Glu
465                 470                 475                 480

Pro Arg Glu Phe Val Glu Asn Ser Glu Cys Ile Gln Cys His Pro Glu
                485                 490                 495

Cys Leu Pro Gln Ala Met Asn Ile Thr Cys Thr Gly Arg Gly Pro Asp
            500                 505                 510

Asn Cys Ile Gln Cys Ala His Tyr Ile Asp Gly Pro His Cys Val Lys
        515                 520                 525

Thr Cys Pro Ala Gly Val Met Gly Glu Asn Asn Thr Leu Val Trp Lys
    530                 535                 540

Tyr Ala Asp Ala Gly His Val Cys His Leu Cys His Pro Asn Cys Thr
545                 550                 555                 560

Tyr Gly Cys Thr Gly Pro Gly Leu Glu Gly Cys Pro Thr Asn Gly Pro
                565                 570                 575

Lys Ile Pro Ser Ile Ala Thr Gly Met Val Gly Ala Leu Leu Leu Leu
            580                 585                 590

Leu Val Val Ala Leu Gly Ile Gly Leu Phe Met Arg Arg Arg His Ile
        595                 600                 605

Val Arg Lys Arg Thr Leu Arg Arg Leu Leu Gln Glu Arg Glu Leu Val
    610                 615                 620

Glu Pro Leu Thr Pro Ser Gly Glu Ala Pro Asn Gln Ala Leu Leu Arg
625                 630                 635                 640

Ile Leu Lys Glu Thr Glu Phe Lys Lys Ile Lys Val Leu Gly Ser Gly
                645                 650                 655

Ala Phe Gly Thr Val Tyr Lys Gly Leu Trp Ile Pro Glu Gly Glu Lys
            660                 665                 670

Val Lys Ile Pro Val Ala Ile Lys Thr Ser Pro Lys Ala Asn Lys Glu
        675                 680                 685

Ile Leu Asp Glu Ala Tyr Val Met Ala Ser Val Asp Asn Pro His Val
    690                 695                 700

Cys Arg Leu Leu Gly Ile Cys Leu Thr Ser Thr Val Gln Leu Ile Thr
705                 710                 715                 720

Gln Leu Met Pro Phe Gly Cys Leu Leu Asp Tyr Val Arg Glu His Lys
                725                 730                 735

Asp Asn Ile Gly Ser Gln Tyr Leu Leu Asn Trp Cys Val Gln Ile Ala
            740                 745                 750

Lys Gly Met Asn Tyr Leu Glu Asp Arg Arg Leu Val His Arg Asp Leu
        755                 760                 765

Ala Ala Arg Asn Val Leu Val Lys Thr Pro Gln His Val Lys Ile Thr
    770                 775                 780

Asp Phe Gly Leu Ala Lys Leu Leu Gly Ala Glu Glu Lys Glu Tyr His
785                 790                 795                 800

Ala Glu Gly Gly Lys Val Pro Ile Lys Trp Met Ala Leu Glu Ser Ile
                805                 810                 815

Leu His Arg Ile Tyr Thr His Gln Ser Asp Val Trp Ser Tyr Gly Val
            820                 825                 830

Thr Val Trp Glu Leu Met Thr Phe Gly Ser Lys Pro Tyr Asp Gly Ile
        835                 840                 845

Pro Ala Ser Glu Ile Ser Ser Ile Leu Glu Lys Gly Glu Arg Leu Pro
    850                 855                 860
```

Gln Pro Pro Ile Cys Thr Ile Asp Val Tyr Met Ile Met Val Lys Cys
865                 870                 875                 880

Trp Met Ile Asp Ala Asp Ser Arg Pro Lys Phe Arg Glu Leu Ile Ile
            885                 890                 895

Glu Phe Ser Lys Met Ala Arg Asp Pro Gln Arg Tyr Leu Val Ile Gln
            900                 905                 910

Gly Asp Glu Arg Met His Leu Pro Ser Pro Thr Asp Ser Asn Phe Tyr
            915                 920                 925

Arg Ala Leu Met Asp Glu Glu Asp Met Asp Asp Val Val Asp Ala Asp
            930                 935                 940

Glu Tyr Leu Ile Pro Gln Gln Gly Phe Phe Ser Ser Pro Ser Thr Ser
945                 950                 955                 960

Arg Thr Pro Leu Leu Ser Ser Leu Ser Ala Thr Ser Asn Asn Ser Thr
            965                 970                 975

Val Ala Cys Ile Asp Arg Asn Gly Leu Gln Ser Cys Pro Ile Lys Glu
            980                 985                 990

Asp Ser Phe Leu Gln Arg Tyr Ser Ser Asp Pro Thr Gly Ala Leu Thr
            995                 1000                1005

Glu Asp Ser Ile Asp Asp Thr Phe Leu Pro Val Pro Glu Tyr Ile Asn
            1010                1015                1020

Gln Ser Val Pro Lys Arg Pro Ala Gly Ser Val Gln Asn Pro Val Tyr
1025                1030                1035                1040

His Asn Gln Pro Leu Asn Pro Ala Pro Ser Arg Asp Pro His Tyr Gln
            1045                1050                1055

Asp Pro His Ser Thr Ala Val Gly Asn Pro Glu Tyr Leu Asn Thr Val
            1060                1065                1070

Gln Pro Thr Cys Val Asn Ser Thr Phe Asp Ser Pro Ala His Trp Ala
            1075                1080                1085

Gln Lys Gly Ser His Gln Ile Ser Leu Asp Asn Pro Asp Tyr Gln Gln
            1090                1095                1100

Asp Phe Phe Pro Lys Glu Ala Lys Pro Asn Gly Ile Phe Lys Gly Ser
1105                1110                1115                1120

Thr Ala Glu Asn Ala Glu Tyr Leu Arg Val Ala Pro Gln Ser Ser Glu
            1125                1130                1135

Phe Ile Gly Ala
        1140

<210> SEQ ID NO 13
<211> LENGTH: 23
<212> TYPE: DNA
<213> ORGANISM: Artificial Sequence
<220> FEATURE:
<223> OTHER INFORMATION: EGFR target site including PAM

<400> SEQUENCE: 13
tcttaattcc ttgatagcga cgg                                          23

<210> SEQ ID NO 14
<211> LENGTH: 73
<212> TYPE: DNA
<213> ORGANISM: Artificial Sequence
<220> FEATURE:
<223> OTHER INFORMATION: KRAS_F Primer

```
<400> SEQUENCE: 14
acactctttc cctacacgac gctcttccga tctacatttt cattattttt attataaggc      60
ctgctgaaaa tga                                                        73

<210> SEQ ID NO 15
<211> LENGTH: 72
<212> TYPE: DNA
<213> ORGANISM: Artificial Sequence
<220> FEATURE:
<223> OTHER INFORMATION: KRAS_R Primer

<400> SEQUENCE: 15
gtgactggag ttcagacgtg tgctcttccg atctttaaaa caagatttac ctctattgtt      60
ggatcatatt cg                                                         72

<210> SEQ ID NO 16
<211> LENGTH: 51
<212> TYPE: DNA
<213> ORGANISM: Artificial Sequence
<220> FEATURE:
<223> OTHER INFORMATION: EGFR_F Primer

<400> SEQUENCE: 16
cactctttcc ctacacgacg ctcttccgat gggactctgg atcccagaag g               51

<210> SEQ ID NO 17
<211> LENGTH: 52
<212> TYPE: DNA
<213> ORGANISM: Artificial Sequence
<220> FEATURE:
<223> OTHER INFORMATION: EGFR_R Primer

<400> SEQUENCE: 17
gtgactggag ttcagacgtg tgctcttccg atcagctgcc agacatgaga aa              52

<210> SEQ ID NO 18
<211> LENGTH: 33
<212> TYPE: DNA
<213> ORGANISM: Artificial Sequence
<220> FEATURE:
<223> OTHER INFORMATION: Phosphothioate primer_F

<400> SEQUENCE: 18
acactctttc cctacacgac gctcttccga tct                                  33

<210> SEQ ID NO 19
<211> LENGTH: 31
<212> TYPE: DNA
<213> ORGANISM: Artificial Sequence
<220> FEATURE:
<223> OTHER INFORMATION: Phosphothioate primer_R

<400> SEQUENCE: 19
gactggagtt cagacgtgtg ctcttccgat c                                    31
```

MUTANT CELL-FREE DNA ISOLATION KIT AND MUTANT CELL-FREE DNA ISOLATION METHOD USING THE SAME

TECHNICAL FIELD

The present disclosure relates to a mutant cell-free DNA isolation kit and a mutant cell-free DNA isolation method using the same. More particularly, the present disclosure relates to a mutant cell-free DNA isolation kit and a mutant cell-free DNA isolation method, both using a CRISPR-Cas system and an exonuclease, for detecting a mutant DNA in a trace amount of a cell-free DNA sample.

BACKGROUND ART

Recently, the importance of early diagnosis of cancer diseases is emerging globally. Thus, researches on methods for early diagnosis of cancer are increasing. However, the current cancer diagnosis methods are mainly invasive methods such as extraction of tissue samples, endoscopy, etc. Because the existing methods involve extraction of a part suspected with a disease and observation with a microscope, they are disadvantageous in terms of patient inconvenience, scarring and long recovery time.

As an alternative to the existing invasive diagnosis and test methods, molecular diagnosis using liquid biopsy is drawing attentions. Because liquid biopsy uses a non-invasive method, the test result can be acquired quickly and multiple analysis of the disease is possible with body fluid, or a liquid biopsy sample, unlike the tissue sample which allows only partial analysis. In particular, liquid biopsy is expected to exhibit excellent efficiency in cancer diagnosis. It is also expected that carcinogenesis, metastasis, etc. can be observed in detail through analysis of cancer cell-derived DNAs existing in body fluid such as blood, urine, etc.

Recently, in the context with liquid biopsy, cell-free DNAs (cfDNAs) which are released from tumors to bloodstream and existing in blood are studied actively. With the advancement in the technologies of isolating and detecting cfDNAs from various biological samples such as blood, plasma, urine, etc., liquid biopsy will become a more effective and trustable tool for monitoring of patients suspected of having cancer. Cancer-derived cfDNAs were identified in 75% of more of patients with progressive pancreatic cancer, ovarian cancer, colon cancer, bladder cancer, gastroesophageal cancer, breast cancer, melanoma, hepatocellular carcinoma, and head and neck cancer, and in 50% of more of patients with kidney cancer, prostate cancer or thyroid cancer. In genetic clinical diagnosis for patients with metastatic colon cancer, cfDNA showed 87.2% sensitivity and 99.2% specificity of KRAS DNA mutations.

Since these researches show the possibility of cancer diagnosis through cfDNA analysis, a cancer-derived DNA in cfDNA is drawing attentions as next-generation biomarker. An initial-phase tumor is diagnosed by identifying tumor-specific DNA mutation from cfDNA derived from a cancer patient. However, there are many technical limitations in early diagnosis of cancer through detection of DNA mutation by analyzing cfDNA in a liquid sample such as blood, urine, etc. (patent document 1). In particular, cfDNA exists in a urine, cerebrospinal fluid, plasma, blood or body fluid sample at a very low concentration and DNA mutation may occur naturally with the aging of cfDNA. Because most of cfDNA present in the plasma of a patient is a wild-type (wt) DNA derived from a normal somatic cell, it is almost impossible to accurately diagnose the presence of a cancer cell-derived DNA from cfDNA with the current sequencing technology. Therefore, in order to diagnose cancer in the early phase with a trace amount of cfDNA, it is necessary to remove normal DNAs and specifically amplify the cancer cell-derived DNA. Thus, a method for improving detection sensitivity and enabling accurate early diagnosis of cancer is necessary.

Meanwhile, the currently developed genome editing based on a Clustered Regularly Interspaced Short Palindrome Repeats (CRISPR) associated endonuclease (Cas) provides a breakthrough technology for target gene knockout, transcriptional activation and gene correction. This technology demonstrates expandability by targeting numerous DNA locations. The CRISPR-Cas system is composed of a guide RNA (gRNA) having a sequence complementary to a targeted DNA or nucleic acid) and the CRISPR enzyme, which is a nuclease capable of cleaving the targeted DNA or nucleic acid. The gRNA and the CRISPR enzyme form the CRISPR-Cas complex, and the formed CRISPR-Cas complex cleaves or modifies the targeted DNA or nucleic acid. The CRISPR system is recently studied a lot with regard to applicability as DNA scissors, as an immune system of prokaryotes and archaea (non-patent document 1, non-patent document 2). However, there has been no attempt to use it for base sequence capturing used in genome sequencing and diagnosis of a disease.

The inventors of the present disclosure have made efforts to find a method for isolating a mutant DNA from cfDNA. As a result, they have completed the present disclosure by using a technology of specifically cleaving a normal DNA from a trace amount of cfDNA using the CRISPR-Cas system and a technology of specifically amplifying a mutant DNA.

(Patent document 1) Korean Patent Publication No. 10-2016-0129523.
(Non-patent document 1) Jinek et al. *Science*, 2012, 337, 816-821.
(Non-patent document 2) Zalatan et al. *Cell*, 2015, 160, 339-350.
(Non-patent document 3) Tian J, Ma K, Saaem I., *Mol Biosyst*, 2009, 5(7), 714-722.
(Non-patent document 4 Michael, L. Metzker, *Nature Reviews Genetics*, 2010, 11, 31-46.

DISCLOSURE

Technical Problem

The present disclosure is directed to providing a mutant cell-free DNA isolation kit.

The present disclosure is also directed to providing a mutant genotype analysis method.

Technical Solution

The present disclosure provides a mutant cell-free DNA isolation kit including: a composition for amplifying a wild-type cell-free DNA and a mutant cell-free DNA, which contains a 5' end-protected primer;
a guide RNA specific for the wild-type cell-free DNA;
a Cas protein for cleaving the wild-type cell-free DNA; and
an exonuclease for removing the wild-type cell-free DNA.

The mutant cell-free DNA may be a DNA including a cancer-specific mutation.

As used herein, the term "cell-free DNA (cfDNA)" refers to a cancer cell-derived DNA which originates from a tumor cell and can be found in a biological sample such as blood, plasma, urine, etc. derived from a cancer patient. It is activated in necrotic or apoptotic normal and/or cancer cells and released into urine, blood, etc. through various cytophysiological processes. Because urine, cerebrospinal fluid (CSF), plasma, blood or body fluid are readily available samples, it can be collected in large quantities via a simple, non-invasive method through repeated sampling.

As used herein, the "CRISPR-Cas system" is composed of a guide RNA (gRNA) having a sequence complementary to a targeted DNA or nucleic acid and the CRISPR enzyme, which is a nuclease capable of cleaving the targeted DNA or nucleic acid. The gRNA and the CRISPR enzyme form the CRISPR-Cas complex, and the formed CRISPR-Cas complex cleaves or modifies the targeted DNA or nucleic acid.

The Cas protein is an essential protein component of the CRISPR-Cas system. When two RNAs called the CRISPR RNA (crRNA) and the transactivating crRNA (tracrRNA) form a complex, an activated endonuclease is formed. The information of the Cas gene and protein is available from the GenBank of the National Center for Biotechnology Information (NCBI), although not being limited thereto.

As used herein, the term "guide RNA" refers to an RNA specific for a target DNA, which is synthesized through transcription of a linear double-stranded DNA or chemical synthesis, is capable of recognizing a target DNA sequence and forming a complex with the Cas protein, and guides the Cas protein to the target DNA. The "target DNA sequence" is a nucleotide sequence present in the target DNA or nucleic acid. Specifically, it is a portion of a nucleotide sequence in a target region of the target DNA or nucleic acid. The "target region" is a region in the target DNA or nucleic acid that can be modified by a guide nucleic acid-editor protein complex.

As used herein, the term "PAM (PAM; protospacer adjacent motif) sequence" refers to sequence with a size of about 3-6 bp, adjacent to a target sequence. It is an essential component recognized by the Cas protein. The CRISPR-Cas complex recognizes the target and PAM sequence and cleaves a specific location.

The kit may be for isolating a mutant cell-free DNA from a wild-type cell-free DNA and a mutant cell-free DNA contained in a liquid sample (blood, plasma, urine, etc.) isolated from an individual suspected with cancer.

The Cas protein may be *Streptococcus pyogenes* Cas9 (SpCas9), *Streptococcus thermophilus* Cas9 (StCas9), *Streptococcus pasteurianus* (SpaCas9), *Campylobacter jejuni* Cas9 (CjCas9), *Staphylococcus aureus* (SaCas9), *Francisella novicida* Cas9 (FnCas9), *Neisseria cinerea* Cas9 (NcCas9), *Neisseria meningitis* Cas9 (NmCas9), or CRISPR-associated endonuclease in *Prevotella* and *Francisella* 1 (Cpf1), although not being necessarily limited thereto.

The information about the Cas protein or gene may be obtained from a publicly available database such as the GenBank of the NCBI (National Center for Biotechnology Information), although not being limited thereto.

The guide RNA may be a dual RNA (dualRNA) or a sgRNA (single-chain RNA) including a crRNA (CRISPR RNA) and a tracrRNA (transactivating crRNA).

The guide RNA may include two or more guide RNAs specific for a plurality of wild-type cell-free DNAs. That is to say, the kit of the present disclosure is a kit capable of multiplexing.

A method for preparing the guide RNA is widely known in the art.

The 5' end-protected primer may have the 5' end of the primer protected with a phosphothioate bond.

The composition for amplifying DNA may be a PCR composition.

In the present disclosure, the term "amplification reaction" refers to a reaction whereby a target nucleic acid sequence is amplified and may be carried out by PCR (polymerase chain reaction). The PCR includes reverse transcription polymerase chain reaction (RT-PCR), multiplex PCR, real-time PCR, assembly PCR, fusion PCR and ligase chain reaction (LCR), although not being limited thereto.

As used herein, the term "primer" refers to a single-stranded oligonucleotide and may also include a ribonucleotide. Specifically, it may be a deoxyribonucleotide. The primer is hybridized or annealed to a region of a template to form a double-stranded structure. In the present disclosure, the primer may be hybridized or annealed to an NGS sequencing adapter sequence. The annealing refers to apposition of an oligonucleotide or a nucleic acid to a template nucleic acid. The apposition allows a polymerase to polymerize a nucleotide, thereby forming a nucleic acid molecule complementary to the template nucleic acid or a portion thereof. The hybridization refers to formation of a duplex structure through pairing of two single-stranded nucleic acids with complementary base sequences. The primer may serve as a starting point of synthesis under a condition where the synthesis of a primer extension product complementary to the template is induced.

The PCR composition may contain, in addition to the 5' end-protected primer specific for the wild-type cell-free DNA and the mutant cell-free DNA, components widely known in the art. Specifically, it may contain a PCR buffer, a dNTP, a DNA polymerase, etc.

As used herein, the term "exonuclease" refers to an enzyme which cleaves a nucleotide sequentially from the 3' end or 5' end of a polynucleotide chain. 3' to 5' exonuclease is an enzyme which cleaves a phosphodiester bond at the 3' end, and 5' to 3' exonuclease is an enzyme which cleaves a phosphodiester bond at the 5' end.

The exonuclease may be any exonuclease known in the art. Specifically, the exonuclease may include 3'→5' exonuclease and/or 5'→3' exonuclease. Specifically, it may be exonuclease III, exonuclease I, T5 exonuclease, T7 exonuclease, exonuclease T, exonuclease V, lambda exonuclease, exonuclease VII, etc. More specifically, it may be exonuclease T7 or exonuclease T (single-stranded specific nuclease), although not being necessarily limited thereto.

When a sample containing a wild-type cell-free DNA and a mutant cell-free DNA is reacted with the composition for amplifying DNA containing the 5' end-protected primer, the ends of the wild-type cell-free DNA and the mutant cell-free DNA are protected with a phosphothioate bond. The protected DNAs are not cleaved by an exonuclease because of the phosphothioate bond.

When a wild-type cell-free DNA is cleaved by a guide RNA and a Cas protein specific for the wild-type cell-free DNA, the unprotected end of the nucleic acid is exposed to an exonuclease. Through this, the wild-type cell-free DNA is removed and only the mutant cell-free DNA is isolated (FIG. 1).

In an example of the present disclosure, when a guide RNA targeting the KRAS gene was used, only the wt KRAS satisfying the 5'-NGG-3' PAM sequence was cleaved selectively by Cas9. It was confirmed through electrophoresis that the wt KRAS DNA cleaved by Cas9 was removed completely by treatment with exonuclease T7 and exonuclease T.

In another aspect, the present disclosure provides a mutant genotype analysis method including:

i) a step of amplifying a wild-type cell-free DNA and a mutant cell-free DNA in an isolated sample containing at least one wild-type cell-free DNA and at least one mutant cell-free DNA using a 5' end-protected primer;

ii) a step of cleaving only the amplified wild-type cell-free DNA by treating with a Cas protein and a guide RNA binding specifically to the wild-type cell-free DNA;

iii) a step of removing only the cleaved wild-type cell-free DNA by treating the sample containing the mutant cell-free DNA and the cleaved cell-free DNA with an exonuclease;

iv) a step of amplifying the mutant cell-free DNA remaining in the sample; and v) a step of analyzing the amplified mutant cell-free DNA.

The isolated sample containing at least one wild-type cell-free DNA and at least one mutant cell-free DNA may be a blood, plasma or urine sample isolated from an individual suspected with cancer.

The mutant cell-free DNA may be a DNA including cancer-specific mutation.

The analysis of the mutant cell-free DNA may be for providing information for diagnosis of cancer.

As used herein, the term "diagnosis" includes to decision of the susceptibility of a subject to a specific disease or disorder, decision of the presence of a specific disease or disorder in a subject, decision of the prognosis of a subject having a specific disease or disorder, or therametrics (e.g., monitoring of the status of a subject in order to provide information for therapeutic effects).

In the present disclosure, the diagnosis may include identification of the onset of cancer and/or prognosis of cancer.

The cancer may be early-stage cancer.

The cancer may be, for example, one or more selected from a group consisting of squamous cell carcinoma (e.g., squamous cell carcinoma of the epithelium), small-cell lung carcinoma, non-small-cell lung carcinoma, lung cancer, peritoneal cancer, colon cancer, bile duct tumor, nasopharyngeal cancer, laryngeal cancer, bronchogenic cancer, oral cancer, osteosarcoma, gallbladder cancer, kidney cancer, leukemia, bladder cancer, melanoma, brain cancer, glioma, brain tumor, skin cancer, pancreatic cancer, breast cancer, liver cancer, bone marrow cancer, esophageal cancer, colon cancer, stomach cancer, cervical cancer, prostate cancer, ovarian cancer, head and neck cancer, and rectal cancer, although not being limited thereto.

The 5' end-protected primer may have the 5' end of the primer protected with a phosphothioate bond.

The Cas protein may be *Streptococcus pyogenes* Cas9 (SpCas9), *Streptococcus thermophilus* Cas9 (StCas9), *Streptococcus pasteurianus* (SpaCas9), *Campylobacter jejuni* Cas9 (CjCas9), *Staphylococcus aureus* (SaCas9), *Francisella novicida* Cas9 (FnCas9), *Neisseria cinerea* Cas9 (NcCas9), *Neisseria meningitis* Cas9 (NmCas9), or CRISPR-associated endonuclease in *Prevotella* and *Francisella* 1 (Cpf1), although not being necessarily limited thereto.

The guide RNA may be a dual RNA (dualRNA) or an sgRNA (single-chain RNA) including a crRNA (CRISPR RNA) and a tracrRNA (transactivating crRNA).

The amplification may be performed by PCR and the PCR condition may be determined based on methods widely known in the art.

Advantageous Effects

A mutant cell-free DNA isolation kit and a mutant cell-free DNA isolation method of the present disclosure use the CRISPR-Cas system and an exonuclease, and allow selective removal of normal somatic cell-derived DNAs, which account for most of cfDNA (>99.9%) in blood. As a result, because only the mutant cell-free DNA (cancer cell-derived DNA) in the cfDNA can be analyzed, it can be usefully used for early diagnosis of cancer.

In addition, the mutant cell-free DNA isolation kit and the mutant cell-free DNA isolation method of the present disclosure provide an effect of allowing the analysis of a trace amount of mutant cell-free DNAs (cancer cell-derived DNAs) existing in cfDNA by removing the normal cell-derived DNAs from the sample.

Furthermore, the present disclosure allows simultaneous detection of two or more oncogenes via a multiplexing system because a guide RNA specific for a plurality of wild-type DNAs.

BRIEF DESCRIPTION OF DRAWINGS

FIG. 1 schematically shows a procedure of amplifying mtDNA (mutant DNA) only by selectively removing wtDNA (wild-type DNA) from a sample according to the present disclosure.

FIGS. 2a and 2b show a result of selectively cleaving wtDNA in a sample using a CRISPR-Cas system according to the present disclosure.

FIGS. 3a and 3b show a result that a DNA cleaved by the CRISPR-Cas system according to the present disclosure is selectively degraded by an exonuclease.

FIG. 4 shows a result of analyzing a sample with KRAS wtDNA removed by treating with a CRISPR-Cas and an exonuclease according to the present disclosure through next-generation base sequencing.

FIG. 5 shows a result of analyzing a sample with KRAS wtDNA removed by treating with a CRISPR-Cas and an exonuclease according to the present disclosure through Sanger sequencing.

FIG. 6 schematically shows a procedure of amplifying multiple cancer-derived DNAs at once by removing multiple target DNAs through multiplexing by treating with CRISPR-Cas and an exonuclease according to the present disclosure.

FIGS. 7a and 7b show a result of confirming that only a target DNA (wtDNA) can be removed selectively using a multiplexing system by treating with a CRISPR-Cas and an exonuclease according to the present disclosure through agarose gel electrophoresis.

FIG. 8 shows a result of analyzing a sample with KRAS wtDNA and EGFR wtDNA removed using a multiplexing system by treating with a CRISPR-Cas and an exonuclease according to the present disclosure through next-generation base sequencing.

FIG. 9 schematically shows a method of removing DNA using a multiplexing system and a Cas9 orthologue according to the present disclosure.

BEST MODE

The CRISPR-Cas system is an endonuclease with very high accuracy, which is capable of selectively cleaving a target DNA. Cas9 orthologues have different PAM site sequences. The PAM sequence is a DNA sequence essential for the recognition of the target DNA by the Cas9 protein.

Even when bound to a guide RNA perfectly complementary to the target DNA, the CRISPR-Cas system does not operate unless the PAM sequence is satisfied. And, if the guide RNA has many DNA sequences non-complementary to the target DNA, the CRISPR-Cas cannot recognize the target DNA normally. In order to identify a cancer gene generated by nucleotide substitution, a guide RNA complementary to a wild-type DNA was designed. The designing of the target of the guide RNA was largely based on two criteria. If the base sequence prior to the occurrence of substitution corresponds to the PAM site, the guide RNA was designed based on the PAM site. Otherwise, if it does not correspond to the PAM site, a mismatch was added to the seed region. The seed region of Cas9 is a region which responds very sensitively to the mismatch between the guide RNA and the target DNA during the recognition of the target DNA. If there is a mismatch of 1-2 nt in the seed region, the target DNA is not recognized clearly.

The guide RNA used in the present disclosure is designed so as to recognize the wild-type DNA selectively.

In the present disclosure, when the target DNA was cleaved by Cas9 and then amplified by PCR, the amplified amount was smaller for the wild-type cell-free DNA cleaved by Cas9 than for the mutant cell-free DNA. However, the detection limit for identifying a trace amount of mutant DNA could not be achieved with a simple method of cleaving the wild-type DNA with Cas9 and conducting PCR for the mutant DNA. Because the fragment of the wild-type DNA cleaved by Cas9 can serve as a primer during PCR, a DNA sequence derived from the wild-type DNA can be included in the finally amplified PCR product. The cleaved DNA fragments intensify the background signal and make it impossible to achieve the detection limit for identifying the trace amount of the cancer-derived DNA (see the left-side box at the bottom of FIG. 1).

However, in the present disclosure, the cleaved fragments of the wild-type DNA, which generate background signals during PCR, are removed to provide sufficient detection ability for a trace amount of the target DNA. When the target DNA is amplified by PCR in the final process of analyzing the trace amount of cfDNA, a primer with the 5' end protected with a phosphothioate bond is used, or an adaptor containing a phosphothioate bond is ligated on both ends of an amplified PCR amplicon. If the phosphodiester bond connecting nucleotides is replaced with the phosphothioate bond, a nuclease cannot cleave the nucleotides having the bond.

If the target DNA with both ends protected with the phosphothioate bond is treated with an exonuclease, the target DNA is not degraded by the exonuclease. However, if the target DNA is cleaved by Cas9, new DNA ends not protected with phosphothioate are exposed to the exonuclease, and the DNAs cleaved by Cas9 are removed by the exonuclease.

That is to say, the DNA cleavage and removal technologies on the present disclosure play a complementary role, enabling the accurate detection of a cancer-derived DNA in a trace amount of cfDNA, which was not possible before.

In an aspect of the present disclosure, it was confirmed that a complex of the SpCas9 protein and the guide RNA allows accurate cleavage of the target DNA satisfying the PAM sequence of 5'-NGG-3'.

In the present disclosure, the mutation of the KRAS gene is a major mutation of the cancer gene, and is an important biomarker for cfDNA. The frequently occurring mutation of KRAS is change of the 12nd amino acid from aspartate to valine due to the substitution of the 35th nucleic acid on the cDNA from G to T. For the mtDNA with the 35th nucleic acid substituted from guanosine to thymidine, the base sequence corresponding to PAM of Cas9 on the substituted target DNA is changed to NGT. SpCas9, which specifically recognizes NGG as a PAM sequence, specifically recognizes wt KRAS only from wt KRAS and mt KRAS (35G>T) and cleaves the DNA (FIG. 2).

Hereinafter, the present disclosure will be described in detail through examples. However, the following examples are for illustrative purposes only and it will be apparent to those of ordinary skill in the art that the scope of the present disclosure is not limited by the examples.

Example 1: Isolation and Purification of SpCas9

For expression of the recombinant *Streptococcus pyogenes* Cas9 (spCas9) protein containing a His×6 tag at the N-terminal, a plasmid having the genetic information of spCas9 (full sequence of the protein including the His×6 tag, SEQ ID NO 1) was transformed into BL21-DE3 competent cells. After IPTG (isopropyl β-D-thiogalactoside) treatment, the BL21-DE3 were cultured at 18° C. for 16 hours. The cells were centrifuged at 5000×g for 15 minutes and then lysed with a lysis buffer containing 50 mM (pH 8) $NaH_2PO_4$, 400 mM NaCl, 10 mM imidazole, 1 mM PMSF, 1 mM DTT, 1% Triton X-100 and 1 mg/mL lysozyme. After sonicating using an ultrasonicator, the cells were centrifuged at 15000×g for 30 minutes and the supernatant was separated from the cell debris. After adding a nickel-nitrilotriacetic acid (Ni-NTA) resin (Invitrogen, Carlsbad, Calif.) to the supernatant and incubating at 4° C. for 1 hour, the Ni-NTA resin was washed repeatedly twice with a washing buffer (50 mM (pH 8) $NaH_2PO_4$, 400 mM NaCl, 20 mM imidazole). Finally, spCas9 was separated from the Ni-NTA resin by adding an elution buffer (50 mM (pH 8) $NaH_2PO_4$, 400 mM NaCl, 250 mM imidazole) to the resin. The buffer containing spCas9 was replaced with a buffer containing 20 mM (pH 7.5) HEPES, 400 mM NaCl, 1 mM DTT and 40% glycerol using an Amicon Ultra centrifugal filter.

Example 2. Synthesis of Guide RNA by In Vitro Transcription

A guide RNA was synthesized in vitro by reacting a DNA template containing guide RNA information and a T7 RNA polymerase in a buffer containing 40 mM Tris-HCl (pH 7.9), 6 mM $MgCl_2$, 10 mM DTT, 10 mM NaCl, 2 mM spermidine, NTP and Rnase inhibitor at 37° C. for 18 hours (SEQ ID NOS 2 and 3). The synthesized guide RNA was purified using an RNA purification kit.

Example 3. In Vitro Cleavage 500 ng of the SpCas9 (hereinafter, denoted as Cas9) isolated and purified according to Example 1 and 100 ng of the guide RNA prepared according to Example 2 were bound at 37° C. for 5 minutes, and then reacted with 150 ng of the wild-type KRAS gene (SEQ ID NO 4) and the mutant KRAS gene (KRAS D12V, SEQ ID NO 6), which are double-stranded DNAs (dsDNAs), in a buffer (50 mM (pH 7.9) potassium acetate, 20 mM Tris-acetate, 10 mM magnesium acetate, 1 mM DTT) at 37° C. for 60 minutes. The information of the KRAS gene and its amino acid sequence is given in Table 1.

TABLE 1

| In-vitro DNA substrate | Sequence |
|---|---|
| SEQ ID NO 4: sequence of wild-type KRAS (2787 nt) | gtttgtttgttttgagatggagtcttactccgtcacccaatctggagtgcagtggcgtgatctgggctc<br>actgcaacctctgcctcccgggttcaagtgattctcctcctcagcctcccagtagctaggactacag<br>gagagcgccaccacgcctgattaattttgtatttttagtagagagagggtttcaccatattggccagg<br>ctggtcttgaactcctggcctcaggtgatccacccgccttggcctctgaaagtgctgggattacaggca<br>tgagccgccgcacccggctttctaatctttatctttttgtgcagcggtgatacaggattatgtattg<br>tactgaacagttaattcggagttctcttggttttagctttattttccccagagattttttttttttt<br>tttttttttgagacggagtcttgctctatcgccaggctggagtgcagtggcgccatctcggctcattgc<br>aacctcggactcctattttccccagagatatttcacacattaaaatgtcgtcaaatattgttcttcttt<br>gcctcagtgtttaaatttttatttccccatgacacaatccagctttatttgacactcattctctcaact<br>ctcatctgattcttactgttaatatttatccaagagaactactgccatgatgctttaaaagttttctg<br>tagctgttgcatattgacttctaacacttagaggtgggggtccactaggaaaactgtaacaataagagt<br>ggagatagctgtcagcaacttttgtgagggtgtgctacagggtgtagagcactgtgaagtctctacatg<br>agtgaagtcatgatatgatcctttgagagcctttagccgccgcagaacagcagtctggctatttagata<br>gaacaacttgattttaagataaaagaactgtctatgtagcatttatgcattttttcttaagcgtcgatgg<br>aggagtttgtaaatgaagtacagttcattacgatacacgtctgcagtcaactggaattttcatgattga<br>attttgtaaggtattttgaaataattttcatataaaggtgagtttgtattaaaaggtactggtggagt<br>atttgatagtgtattaaccttatgtgtgacatgttctaatatagtcacattttcattatttttattata<br>aggcctgctgaaa<u>atgactgaatataaacttgtggtagttggagctggtggcgtaggcaagagtgcctt</u><br><u>gacgatacagctaattcagaatcatttgtggacgaatatgatccaacaatagagg</u>taaatcttgtttt<br>aatatgcatattactggtgcaggaccattctttgatacagataaaggtttctctgaccattttcatgag<br>tacttattacaagataattatgctgaaagttaagttatctgaaatgtacctggtttcaagttatatg<br>taaccattaatatgggaacttacttccttgggagtatgtcagggtccatgatgttcactctctgtgc<br>attttgattggaagtgtatttcagagtttcgtgagagggtagaaatttgtatcctatctggacctaaaa<br>gacaatctttttattgtaactttatttttatgggtttcttggtattgtgacatcatatgtaaaggtta<br>gatttaattgtactagtgaaatataattgttgatggttgattttttaaacttcatcagcagtatttt<br>cctatcttcttctcaacattagagaacctacaactaccggataaattttacaaaatgaattatttgcct<br>aaggtgtggtttatataaaggtactattaccaacttacctttgctttgttgtcatttttaaatttact<br>caaggaaatactaggatttaaaaaaaaaattccttgagtaaatttaaattgttatcatgttttgaggat<br>tattttcagatttttttagtttaatgaaaatttaccaaagtaaagaccagcagcagaatgataagtaaa<br>gacctgtaagacacctgaaggtcatggagtagaacttccatcccaagcagatgaggatttatttaatc<br>tcaaagacctccaggagggacattccccaactgtccttgttaactcattttcagaacatattattag<br>catattttacatgtaatttggatcttcatgttaaatttaacatcagtggagatggaaaataagcatatc<br>gccttgtctttgaaatagcccatatattgttagattgtttcttaggcttcttttaccctgggttaagcagt<br>cctaatactttagcatttattctacatctagtgtactaatttaaaaaaatcagttctgaaaaatttcta<br>agaactttcttcaagttccaagctgtgaaatctagaacaggtcaaagtgccttattaacgtactgtact<br>gtgtagtgtcttgaagagacactttgcgctgaggcaagttctgagggcattgggtggccttgggaagat<br>atttatgcagtttagaacctggagaattgattagataactaatcataaggaaacgtcacatatttttgg<br>tactataaaaaagtggagaaataatgcctatttgcaaagatttgatttaaacatagaaacaactttatt<br>tggcttccaattttaagaatttacagcagtaaaggggaacagtctaattgaagtagactgcctatgcaa<br>tagtctctgtatatttacttttgacaagttaattcaatgtgtactatagttttgtttctttgaagaggt<br>ttgaatagtgcacccattttaatctgt<br>Underline: exon 1 |
| SEQ ID NO 5: amino acid sequence of wild-type KRAS from exon 1 | MTEYKLVVVGAGGVGKSALTIQLIQNHFVDEYDPTIEDSYRKQVVIDGETCLLDILDTAGQEEYSAMRD<br>QYMRTGEGFLCVFAINNTKSFEDIHHYREQIKRVKDSEDVPMVLVGNKCDLPSRTVDTKQAQDLARSYG<br>IPFIETSAKTRQRVEDAFYTLVREIRQYRLKKISKEEKTPGCVKIKKC<br>Underline: KRAS exon 1<br>Shade: G12V mutation |
| SEQ ID NO 6: sequence of mutant KRAS c.G35 > T target (2787 nt) | gtttgtttgttttgagatggagtcttactccgtcacccaatctggagtgcagtggcgtgatctgggctc<br>actgcaacctctgcctcccgggttcaagtgattctcctcctcagcctcccagtagctaggactacag<br>gagagcgccaccacgcctgattaattttgtatttttagtagagagagggtttcaccatattggccagg<br>ctggtcttgaactcctggcctcaggtgatccacccgccttggcctctgaaagtgctgggattacaggca<br>tgagccgccgcacccggctttctaatctttatctttttgtgcagcggtgatacaggattatgtattg<br>tactgaacagttaattcggagttctcttggttttagctttattttccccagagattttttttttttt<br>tttttttttgagacggagtcttgctctatcgccaggctggagtgcagtggcgccatctcggctcattgc<br>aacctcggactcctattttccccagagatatttcacacattaaaatgtcgtcaaatattgttcttcttt<br>gcctcagtgtttaaatttttatttccccatgacacaatccagctttatttgacactcattctctcaact<br>ctcatctgattcttactgttaatatttatccaagagaactactgccatgatgctttaaaagttttctg<br>tagctgttgcatattgacttctaacacttagaggtgggggtccactaggaaaactgtaacaataagagt<br>ggagatagctgtcagcaacttttgtgagggtgtgctacagggtgtagagcactgtgaagtctctacatg<br>agtgaagtcatgatatgatcctttgagagcctttagccgccgcagaacagcagtctggctatttagata<br>gaacaacttgattttaagataaaagaactgtctatgtagcatttatgcattttttcttaagcgtcgatgg<br>aggagtttgtaaatgaagtacagttcattacgatacacgtctgcagtcaactggaattttcatgattga<br>attttgtaaggtattttgaaataattttcatataaaggtgagtttgtattaaaaggtactggtggagt<br>atttgatagtgtattaaccttatgtgtgacatgttctaatatagtcacattttcattatttttattata<br>aggcctgctgaaaatgactgaatataaacttgtggtagttggagctgttggcgtaggcaagagtgcctt<br>gacgatacagctaattcagaatcatttgtggacgaatatgatccaacaatagaggtaaatcttgtttt<br>aatatgcatattactggtgcaggaccattctttgatacagataaaggtttctctgaccattttcatgag<br>tacttattacaagataattatgctgaaagttaagttatctgaaatgtacctggtttcaagttatatg<br>taaccattaatatgggaacttacttccttgggagtatgtcagggtccatgatgttcactctctgtgc<br>attttgattggaagtgtatttcagagtttcgtgagagggtagaaatttgtatcctatctggacctaaaa<br>gacaatctttttattgtaactttatttttatgggtttcttggtattgtgacatcatatgtaaaggtta<br>gatttaattgtactagtgaaatataattgttgatggttgattttttaaacttcatcagcagtatttt<br>cctatcttcttctcaacattagagaacctacaactaccggataaattttacaaaatgaattatttgcct<br>aaggtgtggtttatataaaggtactattaccaacttacctttgctttgttgtcatttttaaatttact<br>caaggaaatactaggatttaaaaaaaaaattccttgagtaaatttaaattgttatcatgttttgaggat |

TABLE 1-continued

| In-vitro DNA substrate | Sequence |
|---|---|
| | tattttcagatttttttagtttaatgaaaatttaccaaagtaaagaccagcagcagaatgataagtaaa<br>gacctgtaagacaccttgaaggtcatggagtagaacttccatcccaagcagatgaggatttatttaatc<br>tcaaagacctccaggaggggacattccccaactgtccttgttaactcattttcagaacatatttattag<br>catattttacatgtaatttggatcttcatgttaaatttaacatcagtggagatggaaaataagcatatc<br>gccttgtctttgaaatagccctatattgttagattgtttcttaggcttctttaccctgggttaagcagt<br>cctaatactttagcatttattctacatctagtgtactaatttaaaaaaatcagttctgaaaaatttcta<br>agaactttcttcaagttccaagctgtgaaatctagaacaggtcaaagtgccttattaacgtactgtact<br>gtgtagtgtcttgaagagacactttgcgctgaggcaagttctgagggcattgggtggccttgggaagat<br>atttatgcagtttagaacctggagaattgattagataactaatcataaggaaacgtcacatattttgg<br>tactataaaaaagtggagaaataatgcctatttgcaaagatttgatttaaacatagaaacaacttattt<br>tggcttccaatttttaagaatttacagcagtaaaggggaacagtctaattgaagtagactgcctatgcaa<br>tagtctctgtatatttacttttgacaagttaattcaatgtgtactatagttttgtttctttgaagaggt<br>ttgaatagtgcacccattttaatctgt<br>Underline: exon 1 |
| SEQ ID NO 7:<br>amino acid<br>sequence of<br>mutant KRAS<br>c.G35 > T | MTEYKLVVVGAVGVGKSALTIQLIQNHFVDEYDPTIEDSYRKQVVIDGETCLLDILDTAGQEEYSAMRD<br>QYMRTGEGFLCVFAINNTKSFEDIHHYREQIKRVKDSEDVPMVLVGNKCDLPSRTVDTKQAQDLARSYG<br>IPFIETSAKTRQRVEDAFYTLVREIRQYRLKKISKEEKTPGCVKIKKC<br>Underline: KRAS exon 1<br>Shade: G12V mutation |
| SEQ ID NO 8:<br>KRAS target site<br>(23 nt, including<br>PAM) | aaacttgtggtagttggagctgg |

The DNA fragments cleaved by Cas9 were electrophoresed on 1.5% agarose gel and then identified by staining with EtBr. As a result, it was confirmed that a complex of the isolated and purified Cas9 protein and the guide RNA precisely cleaves only the target site of the DNA satisfying the PAM sequence of 5'-NGG-3' (see FIGS. 2a and 2b).

The mutation of the KRAS gene, which is one of the major mutations of cancer genes, is an important biomarker that can be detected on cfDNA. In particular, in the mutation of KRAS, the mutation whereby the 35th nucleic acid of the cDNA is changed from G to T, so that the 12nd amino acid of the KRAS protein is replaced from glycine (G) to valine (V) is important (SEQ ID NO 5 and SEQ ID NO 7). For the mtDNA wherein the 35th guanosine is substituted with thymidine, the base sequence corresponding to the PAM of Cas9 on the target DNA is changed to NGT. Cas9, which specifically recognizes NGG as a PAM sequence, recognizes only wt KRAS specifically from wt KRAS and mt KRAS (35G>T) and cleaves the DNA (SEQ ID NO 8).

The guide RNA has a target sequence corresponding to the 1572-nt position on the 2787-nt DNA including the wild-type KRAS gene (SEQ ID NO 4). It was confirmed through electrophoresis that the Cas9 complexed with guide RNA produces a long 1572-nt fragment and a short 1215-nt fragment by cleaving the KRAS gene on the 2787-nt DNA (see top of FIG. 2b and top of FIG. 3b). However, even when the guide RNA was used, the mtKRAS gene wherein the PAM sequence is changed to 5'-NGT-3' was not cleaved by Cas9 (see bottom of FIG. 2b and bottom of FIG. 3b).

Example 4. Selective Removal of Wild-Type Cell-Free DNA Only

Experiment was conducted to investigate whether the wild-type cell-free DNA is degraded selectively by a Cas protein and exonuclease.

Target DNAs (wild-type cell-free DNA and mutant-type cell-free DNA isolated from the blood of a cancer patient) were amplified by PCR using a primer 5'-end protected with a phosphothioate bond (Table 2) and a Phusion polymerase.

After purifying the wild-type DNA (wtDNA) and the mutant DNA (mtDNA) using a PCR purification kit (Qiagen Cat ID: 28104), a DNA sample was prepared by mixing the wtDNA and the mtDNA at a ratio of 90:10 (wtDNA ratio 90%; mtDNA ratio 10%), 99:1 (wtDNA ratio 99%; mtDNA ratio 1%), 99.9:0.1 (wtDNA ratio 99.9%; mtDNA ratio 0.1%), 99.99:0.01 (wtDNA ratio 99.99%; mtDNA ratio 0.01%) or 99.999:0.001 (wtDNA ratio 99.999%; mtDNA ratio 0.001%). 500 ng of SpCas9 and 100 ng of a guide RNA were bound at 37° C. for 5 minutes, and the resulting product was reacted with 100 ng of the purified double-stranded DNA (dsDNA) at 37° C. for 60 minutes in a buffer consisting of 50 mM (pH 7.9) potassium acetate, 20 mM Tris-acetate, 10 mM magnesium acetate and 1 mM DTT (dithiothreitol, reducing agent).

TABLE 2

| Primer name | Sequence(5'-3') |
|---|---|
| KRAS_F<br>(SEQ ID NO 14) | ACACTCTTTCCCTACACGACG<br>CTCTTCCGATCTACATTTTCA<br>TTATTTTTATTATAAGGCCTG<br>CTGAAAATGA |
| KRAS_R<br>(SEQ ID NO 15) | GTGACTGGAGTTCAGACGTGT<br>GCTCTTCCGATCTTTAAAACA<br>AGATTTACCTCTATTGTTGGA<br>TCATATTCG |
| EGFR_F<br>(SEQ ID NO 16) | ACACTCTTTCCCTACACGACG<br>CTCTTCCGATGGGACTCTGGA<br>TCCCAGAAGG |
| EGFR_R<br>(SEQ ID NO 17) | GTGACTGGAGTTCAGACGTGT<br>GCTCTTCCGATCAGCTGCCAG<br>ACATGAGAAA |
| Phosphothioate primer_F<br>(SEQ ID NO 18) | A*C*A*CTCTTTCCCTACACG<br>ACGCTCTTCCGATCT |
| Phosphothioate primer_R<br>(SEQ ID NO 19) | G*A*C*TGGAGTTCAGACGTG<br>TGCTCTTCCGATC |

*phosphothioate bond

After the reaction, reaction was conducted additionally at 37° C. for 60 minutes by adding exonuclease T7 and exonuclease T. The DNA fragments treated with Cas9 and the exonuclease were identified by electrophoresis on 1.5% agarose gel or by Sanger sequencing and next-generation sequencing after PCR amplification.

The 2787-nt DNA including the KRAS gene has both ends protected with phosphothioate bonds (see step 1 in FIG. 3a). The DNA with both ends protected with phosphothioate bonds was not degraded even after being treated with the exonuclease. However, when the DNA was cleaved by Cas9, the unprotected end of the nucleic acid was exposed to the exonuclease and the DNA was degraded (see steps 2 and 3 in FIG. 3a). When the guide RNA targeting the KRAS gene was used, only the wt KRAS gene satisfying the PAM sequence of 5'-NGG-3' was cleaved selectively by Cas9. It was confirmed through electrophoresis that the wt KRAS DNA cleaved by Cas9 was completely removed by treating with exonuclease T7 and exonuclease T (see the top rightmost line in FIG. 3b). However, the mt KRAS DNA not cleaved by Cas9 was not degraded even after treatment with the exonuclease because both ends were protected with phosphothioate bonds (the bottom rightmost line in FIG. 3b).

Example 5. Investigation of Detection Limit for Target DNA

The DNA remaining in trace amounts when the target DNA was removed selectively was identified by sequencing. Experiment was conducted by mixing the wtDNA and the mtDNA at different ratios in order to investigate the detection limit for the DNA in trace amounts. After mixing the wt KRAS DNA and the mt KRAS DNA with both ends were protected with phosphothioate bonds at a ratio of 90:10 (wtDNA ratio 90%; mtDNA ratio 10%), 99:1 (wtDNA ratio 99%; mtDNA ratio 1%), 99.9:0.1 (wtDNA ratio 99.9%; mtDNA ratio 0.1%), 99.99:0.01 (wtDNA ratio 99.99%; mtDNA ratio 0.01%) or 99.999:0.001 (wtDNA ratio 99.999%; mtDNA ratio 0.001%) and then treating with Cas and an exonuclease, the finally obtained sample was subjected to sequencing (see FIG. 4).

As seen from FIG. 4, it was confirmed through NGS sequencing that the ratio of the mtDNA increased even in the sample treated only with Cas9. However, when the initial ratio of the mtDNA in the sample was 1% or lower, the ratio of the finally detected mtDNA was decreased remarkably. Considering that the ratio of the mtDNA in cfDNA is 0.01% or lower in general, it is not easy to identify the presence of the mtDNA when the target DNA is removed with Cas9 only. Thus, experiment was conducted as follows to investigate the detection limit for the target DNA.

When the sample treated with Cas9 and the exonuclease was analyzed by Sanger sequencing, it was found out that the region of KRAS c.35 guanosine was read as thymidine. When treated only with Cas9, the histograms of guanosine and thymidine were observed at the same time in the region corresponding to the 35th nucleic acid in the sample where the initial ratio of mtDNA was 1% (NGS result mtDNA: 44%), and the sequence of mtDNA could not be observed in the sample where the initial ratio of mtDNA was 1% or lower (see Cas_treatment on the left side of FIG. 5). However, when treated with Cas9, exonuclease T and exonuclease T7, the mutant sequence could be observed by Sanger sequencing even in the sample where the initial ratio of mtDNA was 0.01% (see Cas+ExoT+ExoT7_treatment on the right side of FIG. 5).

As seen from FIG. 5, it was confirmed that the presence of mtDNA could be identified clearly through NGS for the sample treated with Cas9, exonuclease T and exonuclease T7 even when the initial ratio of mtDNA in the sample was 0.01% or lower (the detection limit of mtDNA only when Cas9 is used was 1%). Accordingly, in the present disclosure, the detection limit is increased by at least 100 times as compared to the method of cleaving the target DNA using only the Cas9 system.

Example 6. Removal of Various Target DNAs Using Multiplex System

Various target DNAs were removed using a multiplex system as described below. The EGFR sequence is shown in Table 3.

TABLE 3

| In-vitro DNA substrate | Sequence |
|---|---|
| SEQ ID NO 9: sequence of wild-type EGFR (2813 nt) | ctcataagcataagcgcgtgtgatgtgccccaaccaaacgaccgccatgcacaacttccctaccggagt tttcaatccagttaataggcgtggaaacagacatagaaattgtgtttgttgaaaggtagctgttcagtt aaagaacacctgtatcagagcctgtgtttctaccaacttctgtcaagctctgtagagaaggcgtacatt tgtccttccaaatgagctggcaagtgccgtgtcctggcacccaagcccatgccgtggctgctggtcccc ctgctgggcatgtctggcactgcttccagcatggtgagggctgaggtgacccttgtctctgtgttct tgtcccccccagcttgtggagcctcttacacccagtgagaagctcccaaccaagctctcttgaggatc ttgaaggaaactgaattcaaaaagatcaaagtgctgggctcggtgcgttcggcacggtgtataaggta aggtccctggcacaggcctctgggctgggccgcagggcctctcatggtctggtggggagcccagagtcc ttgcaagctgtatatttccatcatctactttactctttgtttcactgagtgtttgggaaactccagtgt ttttcccaagttattgagaggaaatcttttataaccacagtaatcagtggtcctgtgagaccaattcac agaccaaaggcattttatgaaaggggccattgaccttgccatggggtgcagcacagggcgggaggagg gccgcctctcaccgcacggcatcagaatgcagcccagctgaaatgggctcatcttcgtttgcttcttct agatcctcttttgcatgaaatctgatttcagttaggcctagacgcagcatcattaaattctggatgaaat gatccacacggactttataacaggcttacaagcttgagattcttttatctaaataatcagtgtgattc gtggagcccaacagctgcagggctgcggggcgtcacagccccccagcaatatcagccttaggtgcggct ccacagcccagtgtccctcaccttcggggtgcatcgctggtaacatccacccagatcactgggcagca tgtggcaccatctcacaattgccagttaacgtcttccttctctctctgtcataggactctggatccca gaaggtgagaaagttaaaattcccgtcgctatcaaggaattaagagaagcaacatctccgaaagccaac aaggaaatcctcgatgtgagtttctgctttgctgtgtgggggtccatggctctgaacctcaggcccacc ttttctcatgtctggcagctgctctgctctagaccctgctcatctccacatcctaaatgttcactttct atgtctttcccttctagctctagtgggtataactccctcccccttagagacagcactggcctctcccat gctggtatccaccccaaaaggctggaaacaggcaattactggcatctacccagcactagtttcttgaca cgcatgatgagtgagtgctcttggtgagcctggagcatgggtattgttttggtattttttggatgaag aaatggaggcataaagaaattggctgaccccttatatggctgggataggtttaagcccccttgttatttc |

TABLE 3-continued

| In-vitro DNA substrate | Sequence |
|---|---|
| | tgactctgaaacttgcattcaattcactccaccaagttatctcatctttgaaatggcttttttaagg<br>tgcctagaatatgatggcgtgcagtctataaactgttgcccacctctgtactttctctcagaataatt<br>cacattcttctccagtgtctgttgattgttactttgtggaataagttcttggaaaattccacaagatta<br>ttgttatcttcttactaccaattctattgaactttctccacctctctgggcttcccagccagtggt<br>gggaagatgctggctggagtctgacagagcctcttctacactggcctgggcttgctgtgagttggtgga<br>aacctttgctcttgtcccaacacagagcaagtgaaagaggaggtcaagggctcaggcagcggactagg<br>gaagcagaatcgaggaaaaggaaaaatggctgacttattacctcaaaactctagagaatttagttgatc<br>ttacagccaagaaggacaaaagccagagagtaatatcctccgcctcatgtctaacccacagaatacata<br>gcaagtaaagagaacatgggcctttataaaaatgtcttaagatacaatttttttaattggaggaaatcta<br>cagtttaattttctctgggcagcttttcttcctttttattatagtaggggaaatcccatgttgatatact<br>tctaaatgaaagatgatgaattgatataatacaataaaaaaatctgtaaaattgatgatatacttatcaa<br>gaaaaattagctttcatttttaacggtttacaaattgagtcaagtcctagtaacaaaatgttaagtctat<br>taacataaccacaagaaatacaggaagacgggcaatctgtgaagcctttcacttacaatctctggcccc<br>tcacctgtgctgtgtaggaaaatctttgtgcacaatttgcttccttaattcattttttattcattcaac<br>acattctaataaattatacaaaatcatgttgaaatgtgaatttcagtggtatttataaatgcagtgtga<br>ggagggtttggatgtattctaagacaatagttgtgctttgggaaggaagcagtgttcactgaaaagtgc<br>ccccaggaccttttaattggaggaaatatgcttctgtggagttggaaatgggg<br>Underline: exon |
| SEQ ID NO 10:<br>amino acid<br>sequence of wild-<br>type EGFR | MRPSGTAGAALLALLAALCPASRALEEKKVCQGTSNKLTQLGTFEDHFLSLQRMFNNCEVVLGNLEITY<br>VQRNYDLSFLKTIQEVAGYVLIALNTVERIPLENLQIIRGNMYYENSYALAVLSNYDANKTGLKELPMR<br>NLQEILHGAVRFSNNPALCNVESIQWRDIVSSDFLSNMSMDFQNHLGSCQKCDPSCPNGSCWGAGEENC<br>QKLTKIICAQQCSGRCRGKSPSDCCHNQCAAGCTGPRESDCLVCRKFRDEATCKDTCPPLMLYNPTTYQ<br>MDVNPEGKYSFGATCVKKCPRNYVVTDHGSCVRACGADSYEMEEDGVRKCKKCEGPCRKVCNGIGIGEF<br>KDSLSINATNIKHFKNCTSISGDLHILPVAFRGDSFTHTPPLDPQELDILKTVKEITGFLLIQAWPENR<br>TDLHAFENLEIIRGRTKQHGQFSLAVVSLNITSLGLRSLKEISDGDVIISGNKNLCYANTINWKKLFGT<br>SGQKTKIISNRGENSCKATGQVCHALCSPEGCWGPEPRDCVSCRNVSRGRECVDKCNLLEGEPREFVEN<br>SECIQCHPECLPQAMNITCTGRGPDNCIQCAHYIDGPHCVKTCPAGVMGENNTLVWKYADAGHVCHLCH<br>PNCTYGCTGPGLEGCPTNGPKIPSIATGMVGALLLLLVVALGIGLFMRRRHIVRKRTLRRLLQERELVE<br>PLTPSGEAPNQALLRILKETEFKKIKVLGSGAFGTVYKGLWIPEGEKVKIPVAIKELREATSPKANKEI<br>LDEAYVMASVDNPHVCRLLGICLTSTVQLITQLMPFGCLLDYVREHKDNIGSQYLLNWCVQIAKGMNYL<br>EDRRLVHRDLAARNVLVKTPQHVKITDFGLAKLLGAEEKEYHAEGGKVPIKWMALESILHRIYTHQSDV<br>WSYGVTVWELMTFGSKPYDGIPASEISSILEKGERLPQPPICTIDVYMIMVKCWMIDADSRPKFRELII<br>EFSKMARDPQRYLVIQGDERMHLPSPTDSNFYRALMDEEDMDDVVDADEYLIPQQGFFSSPSTSRTPLL<br>SSLSATSNNSTVACIDRNGLQSCPIKEDSFLQRYSSDPTGALTEDSIDDTFLPVPEYINQSVPKRPAGS<br>VQNPVYHNQPLNPAPSRDPHYQDPHSTAVGNPEYLNTVQPTCVNSTFDSPAHWAQKGSHQISLDNPDYQ<br>QDFFPKEAKPNGIFKGSTAENAEYLRVAPQSSEFIGA<br>Underline: EGFR exon<br>Shade: Del. E746-A750 |
| SEQ ID NO 11:<br>mutant EGFR<br>c.2235-2249 del.<br>(2798 nt) | ctcataagcataagcgcgtgtgatgtgcccaaccaaacgaccgccatgcacaacttccctaccggagt<br>tttcaatccagttaataggcgtggaaacagacatagaaattgtgtttgttgaaaggtagctgttcagtt<br>aaagaacacctgtatcagagcctgtgtttctaccaactctgtcaagctctgtagagaaggcgtacatt<br>tgtccttccaaatgagctggcaagtgccgtgtcctggcacccaagcccatgcgtggctgctggtcccc<br>ctgctgggccatgtctggcactgcttttccagcatggtgagggctgaggtgacccttgtctctgtgttct<br>tgtccccccagcttgtggagcctcttacacccagtggagaagctcccaaccaagctctcttgaggatc<br>ttgaaggaaactgaattcaaaaagatcaaagtgctgggctccggtgcgttcggcacggtgtataaggta<br>aggtccctggcacaggcctctgggctgggccgcagggcctctcatggtctggtggggagcccagagtcc<br>ttgcaagctgtatatttccatcatctactttactctttgtttcactgagtgtttgggaaactccagtgt<br>ttttcccaagttattgagaggaaatcttttataaccacagtaatcagtggtcctgtgagaccaattcac<br>agaccaaaggcatttttatgaaagggccattgaccttgccatggggtgcagcacagggcgggaggagg<br>gccgcctctcaccgcacggcatcagaatgcagcccagctgaaatgggctcatcttcgtttgcttcttct<br>agatcctctttgcatgaaatctgatttcagttaggcctagacgcagcatcattaaattctggatgaaat<br>gatccacacggactttataacaggctttacaagcttgagattcttttatctaaataatcagtgtgattc<br>gtggagcccaacagctgcagggctgcggggcgtcacagcccccagcaatatcagccttaggtgcggct<br>ccacagcccagtgtccctcaccttcgggtgcatcgctggtaacatccaccagatcactgggcagca<br>tgtggcaccatctcacaattgccagttaacgtcttccttctctctgtcatagggactctggatccca<br>gaaggtgagaaagttaaaattcccgtcgctatcaagacatctccgaaagccaacaaggaaatcctgat<br>gtgagtttctgctttgctgtgtgggggtccatggctctgaacctcaggcccacctttctcatgtctgg<br>cagctgctctgctctagaccctgctcatctccacatcctaagtttcactttctatgtcttttccctttc<br>tagctctagtgggtataactcctcccttagagacagcactggcctctccatgctggtatccacccc<br>aaaaggctggaaacaggcaattactggcatctacccagcactagtttcttgacacgcatgatgagtgag<br>tgctcttggtgagcctggagcatgggtattgtttttggtattttttggatgaagaaatggaggcataaa<br>gaaattggctgaccctttatatggctgggataggttttaagccccttgttatttctgactctgaaacttg<br>cattcaattcactccaccaagttatctcatctttgaaatggcttttttaaaggtgcctagaatatgat<br>ggcgtgcagtctataaactgttgcccacctctgtactttctctcagaataattcacattcttctccag<br>tgtctgttgattgttactttgtggaataagttcttggaaaattccacaagattattgttatcttcttac<br>taccaattctattgaactttctccacctctctgggcttccccagccagtggtgggaagatgctggctggt<br>ggagtctgacagagcctcttctacactggcctgggcttgctgtgagttggtggaaactttgctcttgt<br>cccaacacagagcaagtgaaagaggaggtcaagggctcaggcagcggactagggaagcagaatcgagg<br>aaaaggaaaaatggctgacttattacctcaaaactctagagaatttagttgatcttacagccaagaagg<br>acaaaagccagagagtaatatcctccgcctcatgtctaacccacagaatacatagcaagtaaagagaac<br>atgggcctttataaaaatgtcttaagatacaatttttttaattggaggaaatctacagtttaattttctc<br>tgggcagcttttcttcctttttattatagtaggggaaatcccatgttgatatacttctaaatgaaagatg<br>atgaattgatataatacaataaaaaaatctgtaaaattgatgatatacttatcaagaaaaattagctttc<br>attttaacggtttacaaattgagtcaagtcctagtaacaaaatgttaagtctattaacataaccacaag<br>aaatacaggaagacgggcaatctgtgaagcctttcacttacaatctctggcccctcacctgtgctgtgt |

TABLE 3-continued

| In-vitro DNA substrate | Sequence |
|---|---|
| | aggaaaatctttgtgcacaatttgcttccttaattcatttttttattcattcaacacattctaataaatt<br>atacaaaatcatgttgaaatgtgaatttcagtggtatttataaatgcagtgtgaggagggtttggatgt<br>attctaagacaatagttgtgctttgggaaggaagcagtgttcactgaaaagtgcccccaggaccttttta<br>attggaggaaatatgcttctgtggagttggaaatgggg |
| SEQ ID NO 12:<br>amino acid<br>sequence of mutant<br>EGFR c.2235-2249<br>del. | MRPSGTAGAALLALLAALCPASRALEEKKVCQGTSNKLTQLGTFEDHFLSLQRMFNNCEVVLGNLEITY<br>VQRNYDLSFLKTIQEVAGYVLIALNTVERIPLENLQIIRGNMYYENSYALAVLSNYDANKTGLKELPMR<br>NLQEILHGAVRFSNNPALCNVESIQWRDIVSSDFLSNMSMDFQNHLGSCQKCDPSCPNGSCWGAGEENC<br>QKLTKIICAQQCSGRCRGKSPSDCCHNQCAAGCTGPRESDCLVCRKFRDEATCKDTCPPLMLYNPTTYQ<br>MDVNPEGKYSFGATCVKKCPRNYVVTDHGSCVRACGADSYEMEEDGVRKCKKCEGPCRKVCNGIGIGEF<br>KDSLSINATNIKHFKNCTSISGDLHILPVAFRGDSFTHTPPLDPQELDILKTVKEITGFLLIQAWPENR<br>TDLHAFENLEIIRGRTKQHGQFSLAVVSLNITSLGLRSLKEISDGDVIISGNKNLCYANTINWKKLFGT<br>SGQKTKIISNRGENSCKATGQVCHALCSPEGCWGPEPRDCVSCRNVSRGRECVDKCNLLEGEPREFVEN<br>SECIQCHPECLPQAMNITCTGRGPDNCIQCAHYIDGPHCVKTCPAGVMGENNTLVWKYADAGHVCHLCH<br>PNCTYGCTGPGLEGCPTNGPKIPSIATGMVGALLLLLVVALGIGLFMRRRHIVRKRTLRRLLQERELVE<br>PLTPSGEAPNQALLRILKETEFKKIKVLGSGAFGTVYKGLWIPEGEKVKIPVAIKTSPKANKEILDEAY<br>VMASVDNPHVCRLLGICLTSTVQLITQLMPFGCLLDYVREHKDNIGSQYLLNWCVQIAKGMNYLEDRRL<br>VHRDLAARNVLVKTPQHVKITDFGLAKLLGAEEKEYHAEGGKVPIKWMALESILHRIYTHQSDVWSYGV<br>TVWELMTFGSKPYDGIPASEISSILEKGERLPQPPICTIDVYMIMVKCWMIDADSRPKFRELIIEFSKM<br>ARDPQRYLVIQGDERMHLPSPTDSNFYRALMDEEDMDDVVDADEYLIPQQGFFSSPSTSRTPLLSSLSA<br>TSNNSTVACIDRNGLQSCPIKEDSFLQRYSSDPTGALTEDSIDDTFLPVPEYINQSVPKRPAGSVQNPV<br>YHNQPLNPAPSRDPHYQDPHSTAVGNPEYLNIVQPTCVNSTFDSPAHWAQKGSHQISLDNPDYQQDFFP<br>KEAKPNGIFKGSTAENAEYLRVAPQSSEFIGA<br>Underline: EGFR exon<br>Del. E746-A750 |
| SEQ ID NO 13:<br>EGFR target site<br>(23 nt,<br>including PAM) | tcttaattccttgatagcga<u>cgg</u> |

Several target DNAs were amplified by PCR using a primer 5'-end protected with a phosphothioate bond (Table 2) and a Phusion polymerase. A target DNA sample was prepared by mixing KRAS DNA and EGFR DNA, which were separated and purified using a PCR purification kit, at a ratio of 1:1. 500 ng of Cas9 and 50 ng of guide RNAs targeting KRAS and EGFR (SEQ ID NO 3) were bound by mixing for 5 minutes. The resulting product was reacted with 100 ng of the purified target DNA sample at 37° C. for 60 minutes in a buffer consisting of 50 mM (pH 7.9) potassium acetate, 20 mM Tris-acetate, 10 mM magnesium acetate and 1 mM DTT.

After the reaction with Cas9, reaction was conducted additionally at 37° C. for 60 minutes by adding exonuclease T7 and exonuclease T. The DNA fragments treated with Cas9 and the exonuclease were identified by electrophoresis on 1.5% agarose gel or by Sanger sequencing and next-generation sequencing after PCR amplification.

When the guide RNA targeting KRAS DNA and the guide RNA targeting EGFR DNA were mixed and bound to Cas9, it was confirmed that each target DNA of a mixture of wt KRAS DNA (2787 nt) and wt EGFR DNA (2813 nt) at a ratio of 1:1 was cleaved by each guide RNA, and that only the cleaved DNAs were removed completely by the exonuclease through electrophoresis (see middle of FIG. 7b). On the contrary, the DNA sample wherein mt KRAS and mt EGFR were mixed at a ratio of 1:1 was not cleaved by Cas9 and was not degraded by the exonuclease (see bottom of FIG. 7b).

As descried above, it was confirmed through electrophoresis that several target DNAs can be removed simultaneously by using a multiplexing system using guide RNAs targeting different DNAs. Also, it was confirmed that several DNAs in trace amounts can be identified by NGS.

Example 7. Investigation of Detection Limit for Various Target DNAs Using Multiplexing System The detection limit of a multiplexing system was investigated by NGS analysis using DNA samples obtained by mixing wtDNA and mtDNA for the KRAS gene and the EGFR gene at different ratios. After mixing wt KRAS DNA, wt EGFR DNA, mt KRAS DNA and mt EGFR DNA with both ends protected with phosphothioate bonds at ratios of 90:10 (KRAS mtDNA ratio: 10%, EGFR mtDNA ratio: 10%, wt KRAS DNA ratio: 90%, wt EGFR DNA ratio: 90%), 99:1 (KRAS mtDNA ratio: 1%, EGFR mtDNA ratio: 1%, wt KRAS DNA ratio: 99%, wt EGFR DNA ratio: 99%), 99.9:0.1 (KRAS mtDNA ratio: 0.1%, EGFR mtDNA ratio: 0.1%, wt KRAS DNA ratio: 99.9% wt EGFR DNA ratio: 99.9%), 99.99:0.01 (KRAS mtDNA ratio: 0.01%, EGFR mtDNA ratio: 0.01%, wt KRAS DNA ratio: 99.99%, wt EGFR DNA ratio: 99.99%), 99.999:0.001 (KRAS mtDNA ratio: 0.001%, EGFR mtDNA ratio: 0.001%, wt KRAS DNA ratio: 99.999%, wt EGFR DNA ratio: 99.999%) and treating with Cas9 and an exonuclease, the finally obtained sample was subjected to sequencing.

As in the experiment using the guide RNA for KRAS only (experiment for a single target DNA), the mutant sequence could not be detected normally with the multiplexing system in the sample wherein 1% or less mtDNA was present when only Cas9 was used. However, when treated with Cas9 and the exonuclease together, the mtDNA could be detected effectively with the multiplexing system (see FIG. 8 and FIG. 9).

Referring to FIG. 9, Cas9 orthologues recognize PAM of different sequences. spCas9 can cleave only the target DNA having the 5'-NGG-3' sequence near the 3' end. The NGG base sequence on the DNA is called the PAM sequence of spCas9. The PAM sequences of nmCas9, saCas9, cjCas9, AsCpf1 and FnCpf1 are recognized respectively as 5'-NNNGMTT-3', 5'-NNGRRT-3', 5'-NNNVRYAC-3', 5'-TTTN-3' and 5'-KYTV-3'. The different Cas9 orthologues can operate normally only when the PAM sequence is satisfied. If the Cas9 orthologue is used for multiplexing, the limitation of the variety of targetable DNAs due to the limitation of PAM sequence can be overcome. As shown in the figure, various cancer mutations can be detected beyond the limitation of the genes that can be targeted with spCsa9 by using various Cas9 orthologues.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A mutant cell-free DNA isolation kit comprising:
   a composition for amplifying a wild-type cell-free DNA and a mutant cell-free DNA, which comprises a 5' end-protected primer which has the 5' end of the primer protected with a phosphothioate bond;
   a guide RNA specific for the wild-type cell-free DNA;
   a Cas protein for cleaving the wild-type cell-free DNA; and
   exonuclease T7 and exonuclease T for removing the wild-type cell-free DNA.

2. The mutant cell-free DNA isolation kit according to claim 1, wherein
   the mutant cell-free DNA is a DNA comprising a cancer-specific mutation, and the kit is for isolating a mutant cell-free DNA from a wild-type cell-free DNA and a mutant cell-free DNA comprised in a blood, plasma or urine sample isolated from an individual suspected with cancer.

3. The mutant cell-free DNA isolation kit according to claim 1, wherein the Cas protein is *Streptococcus pyogenes* Cas9 (SpCas9), *Streptococcus thermophilus* Cas9 (StCas9), *Streptococcus pasteurianus* (SpaCas9), *Campylobacter jejuni* Cas9 (CjCas9), *Staphylococcus aureus* (SaCas9), *Francisella novicida* Cas9 (FnCas9), *Neisseria cinerea* Cas9 (NcCas9), *Neisseria meningitis* Cas9 (NmCas9), or CRISPR-associated endonuclease in *Prevotella* and *Francisella* 1 (Cpf1).

4. The mutant cell-free DNA isolation kit according to claim 1, wherein the guide RNA is a dual RNA (dualRNA) or an sgRNA (single-chain RNA) comprising a crRNA (CRISPR RNA) and a tracrRNA (trans-activating crRNA).

5. The mutant cell-free DNA isolation kit according to claim 1, wherein the guide RNA comprises two or more guide RNAs specific for a plurality of wild-type cell-free DNAs, and the kit is for isolating two or more mutant cell-free DNA simultaneously.

6. The mutant cell-free DNA isolation kit according to claim 1, wherein the composition for amplifying DNA is a PCR composition.

7. A mutant genotype analysis method comprising:
i) a step of amplifying a wild-type cell-free DNA and a mutant cell-free DNA in an isolated sample comprising at least one wild-type cell-free DNA and at least one mutant cell-free DNA using a 5' end-protected primer which has the 5' end of the primer protected with a phosphothioate bond;
ii) a step of cleaving only the amplified wild-type cell-free DNA by treating with a Cas protein and a guide RNA recognizing specifically to the wild-type cell-free DNA;
iii) a step of removing only the cleaved wild-type cell-free DNA by treating the sample comprising the mutant cell-free DNA and the cleaved cell-free DNA with exonuclease T7 and exonuclease T;
iv) a step of amplifying the mutant cell-free DNA remaining in the sample; and
v) a step of analyzing the amplified mutant cell-free DNA.

8. The mutant genotype analysis method according to claim 7, wherein the isolated sample comprising at least one wild-type cell-free DNA and at least one mutant cell-free DNA is a blood, plasma or urine sample isolated from an individual suspected with cancer.

9. The mutant genotype analysis method according to claim 7, wherein
the mutant cell-free DNA is a DNA comprising cancer-specific mutation, and
the analysis of the mutant cell-free DNA is for providing information for diagnosis of cancer.

10. The mutant genotype analysis method according to claim 7, wherein the Cas protein is *Streptococcus pyogenes* Cas9 (SpCas9), *Streptococcus thermophilus* Cas9 (StCas9), *Streptococcus pasteurianus* (SpaCas9), *Campylobacter jejuni* Cas9 (CjCas9), *Staphylococcus aureus* (SaCas9), *Francisella novicida* Cas9 (FnCas9), *Neisseria cinerea* Cas9 (NcCas9), *Neisseria meningitis* Cas9 (NmCas9), or CRISPR-associated endonuclease in *Prevotella* and *Francisella* 1 (Cpf1).

11. The mutant genotype analysis method according to claim 7, wherein the guide RNA is a dual RNA (dualRNA) or an sgRNA (single-chain RNA) comprising a crRNA (CRISPR RNA) and a tracrRNA (transactivating crRNA).

12. The mutant genotype analysis method according to claim 7, wherein the amplification is performed by PCR.

\* \* \* \* \*